United States Patent [19]
van Duyl

[11] Patent Number: 5,617,876
[45] Date of Patent: Apr. 8, 1997

[54] APPARATUS FOR EXAMINING THE FUNCTIONING OF BODY STRUCTURES COMPRISING SMOOTH MUSCLE WALLS

[75] Inventor: Wilhelmus A. van Duyl, Rotterdam, Netherlands

[73] Assignee: LES Enterprises Laborie, Inc., Quebec, Canada

[21] Appl. No.: 307,432

[22] Filed: Sep. 19, 1994

[51] Int. Cl.$^6$ ...................................................... A61B 5/103
[52] U.S. Cl. ............................................................. 128/780
[58] Field of Search ................................. 128/774, 778, 128/780; 606/138

[56] References Cited

U.S. PATENT DOCUMENTS

| | | | |
|---|---|---|---|
| 3,480,003 | 11/1969 | Crites | 128/780 |
| 4,561,450 | 12/1985 | Bryant | 128/780 |
| 4,809,710 | 3/1989 | Williamson | 128/780 |
| 5,109,870 | 5/1992 | Silny et al. | 128/780 |

OTHER PUBLICATIONS

W. A. van Duyl, et al., Neurourology and Urodynamics 9:547–50 (1990).
W. A. van Duyl, et al., Urol. Int. 33:31–39 (1978).
D. J. Griffiths, et al., Med. & Biol. Eng. & Comput., 1979, 17, 281–290.
R. van Mastrigt, et al., Med. & Biol. Eng. & Comput., 1978, 16, 471–482.
W. A. van Duyl, Automedica, 1983, vol. 4, 233–240.
W. A. van Duyl, Neurourology and Urodynamics, 4:275–283 (1985).
R. M. Potjer, et al., Am. J. Physiol., 257, R781–R787 (1989).
R. M. Levin, et al., J. Urology, 136, 517–521 (1986).
F. Plum, et al., AMA Archives of Neurology, 2, 487–496 (1960).
D.J. Griffiths, et al., Am. J. Physiol., 251, R225–R230 (1986).
F. Plum, AMA Archives of Neurology, 2, 497–503 (1960).
A.H. Hoffman, et al., J. Biomechanics, vol. 12, No. 10, 795–800 (1984).
A.D. Drake, et al., IEEE Trans. Biomed. Eng., BME–31, No. 7, 507–11 (1984).
W.A. van Duyl, Neurourology and Urodynamics 4:301–307 (1985).
B.L.R.A. Coolsaet, et al., Neurourology and Urodynamics 12:463–471 (1993).
C.P. Bates, et al., Brit. J. Urology, 53, 333–35 (1981).
D.J. Griffiths, et al., Neurourology and Urodynamiccs, 1:187–92 (1982).

(List continued on next page.)

*Primary Examiner*—Max Hindenburg
*Attorney, Agent, or Firm*—Sherman and Shalloway

[57] ABSTRACT

An apparatus for measuring the micromotion of the wall of a hollow organ comprises: a catheter having a first end and a second end; an inflatable balloon disposed over the first end of the catheter with the balloon being fluid tightly sealed to the catheter at a position intermediate the first and second ends thereof; at least four electrodes affixed to an inner surface of the balloon, the electrodes being spaced apart from one another when the inflatable balloon is at least partially inflated; and a respective electrically conductive lead electrically connected to each of the electrodes, each lead having an electrically insulating cover thereover and each lead passing through said catheter and extending beyond the second end thereof. In use, the catheter with the deflated balloon attached is brought into the hollow organ, e.g., the bladder, and then the balloon is at least partially inflated with a liquid having a predetermined electrical resistivity. The wall of the balloon is thus pressed against the wall of the organ so that the electrodes will move with movement of the organ wall. Movement of the organ wall causes movement of the electrodes which produces a variation in the resistance between the electrodes, which is measured and compared to a calibration of the apparatus to determine the motion of the wall.

7 Claims, 27 Drawing Sheets

OTHER PUBLICATIONS

P. Abrams, Neurourology and Urodynamics, 4:317–328 (1985).

B. Puers, Biotelemetry IX, pp. 155–158 (1987).

E.S.C. van Waalwijk van Doorn, Biotelemetry IX, pp. 159–160 (1987).

R.G. LaGrange, Investigative Urology, 9, No. 1, pp. 64–81 (1971).

J.A. Woltjen, et al., IEEE Trans. Biomed. Eng., Jul. 1973, pp. 295–299.

B.L.R.A. Coolsaet, et al., Neurourology and Urodynamics 4:259–261 (1985).

B.L.R.A. Coolsaet, et al., Neurourology and Urodynamics 7:541–61 (1988).

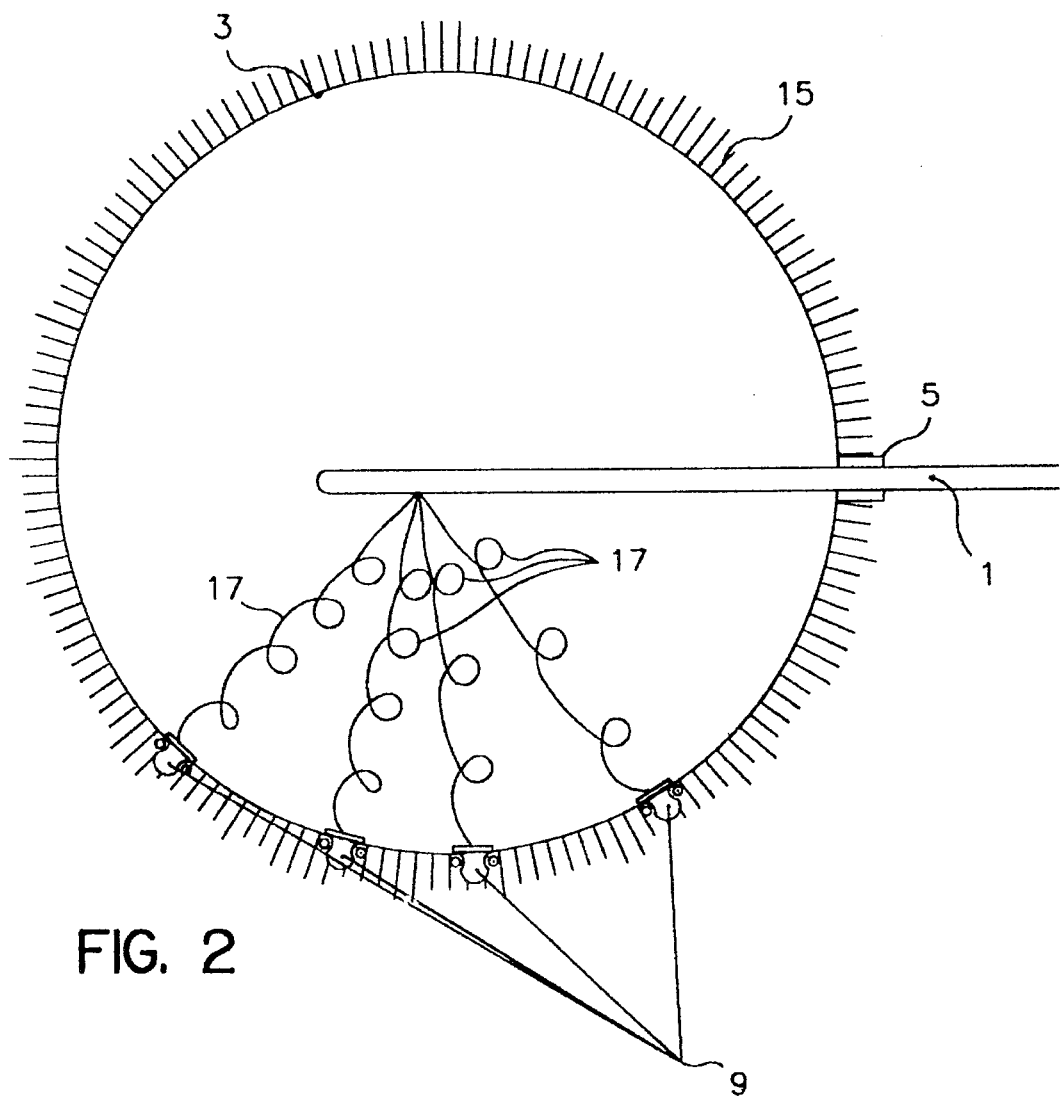
FIG. 2
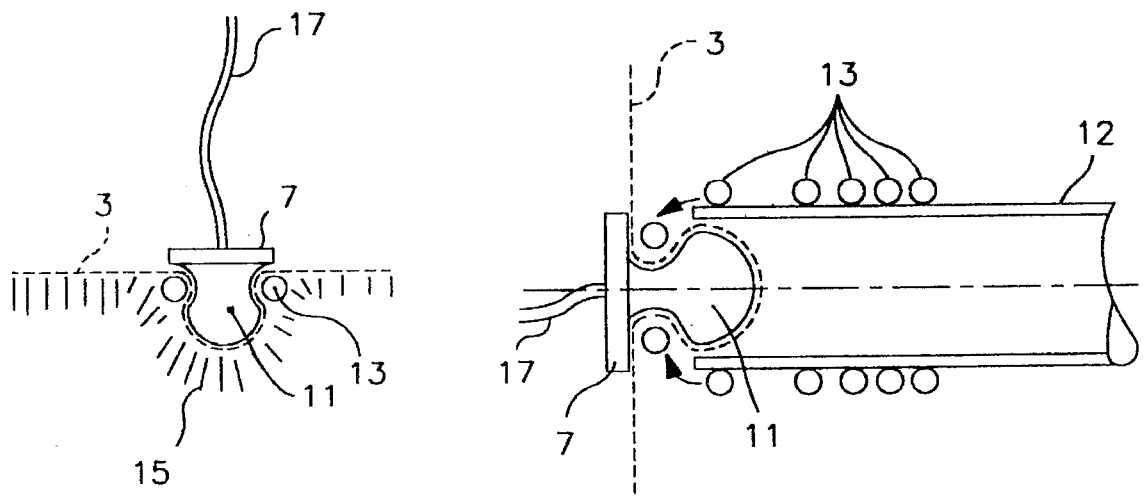
FIG. 3A
FIG. 3B

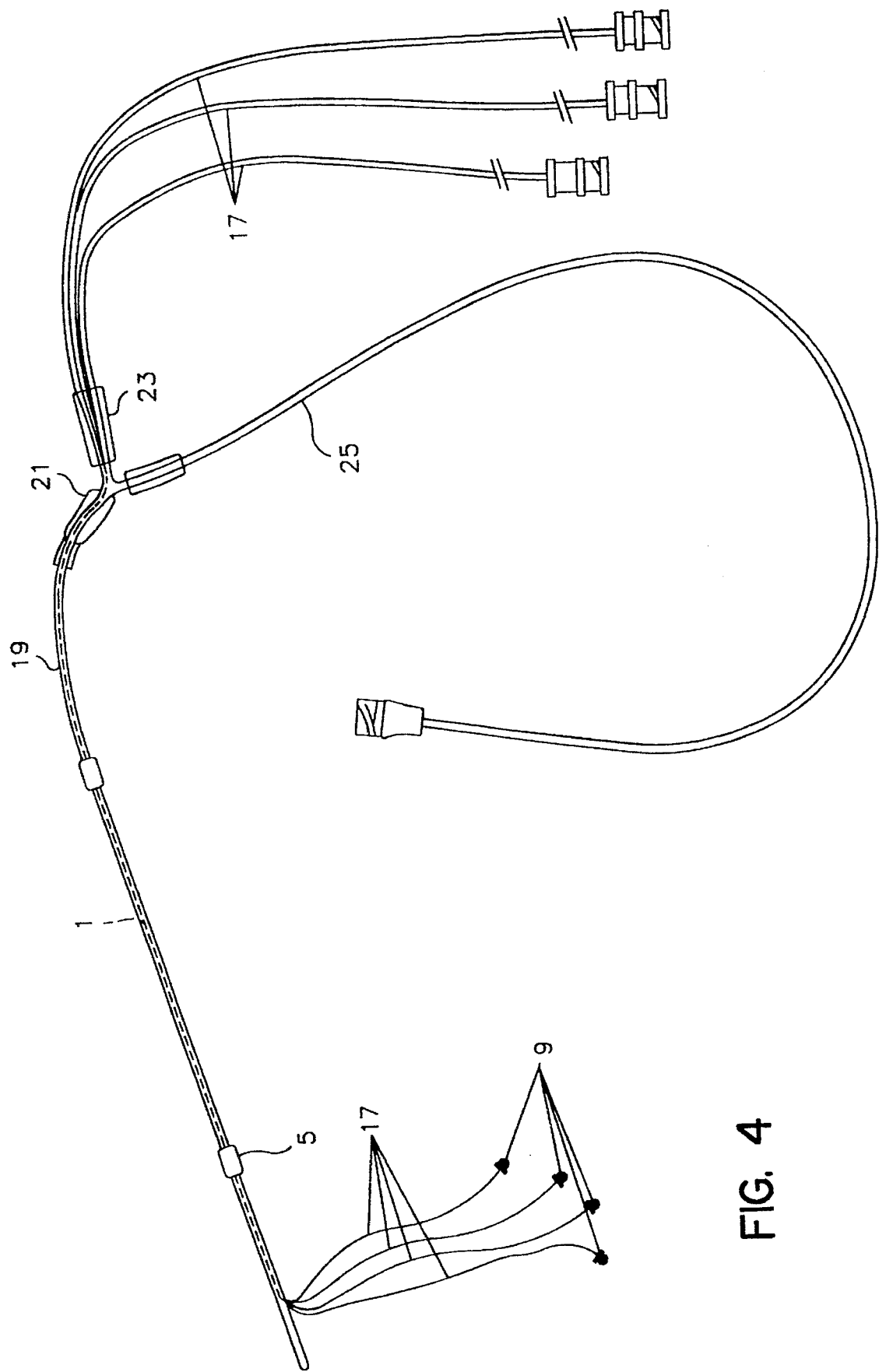

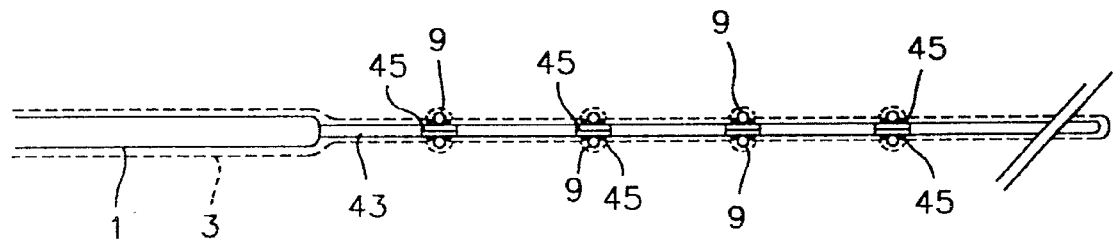
FIG. 7
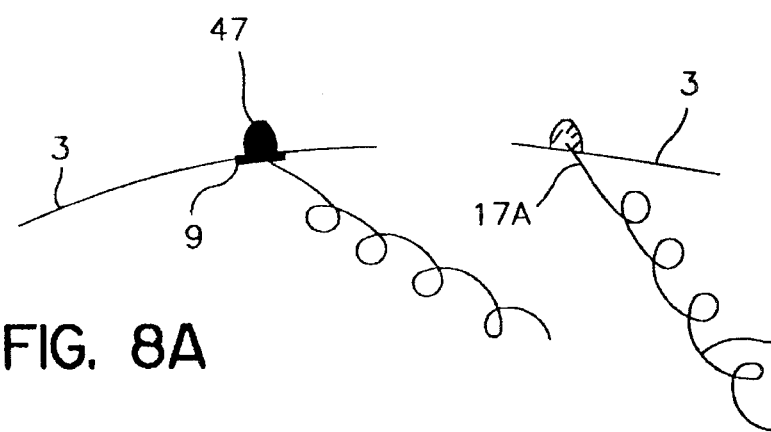
FIG. 8A
FIG. 8B

Exp 1 VITRO

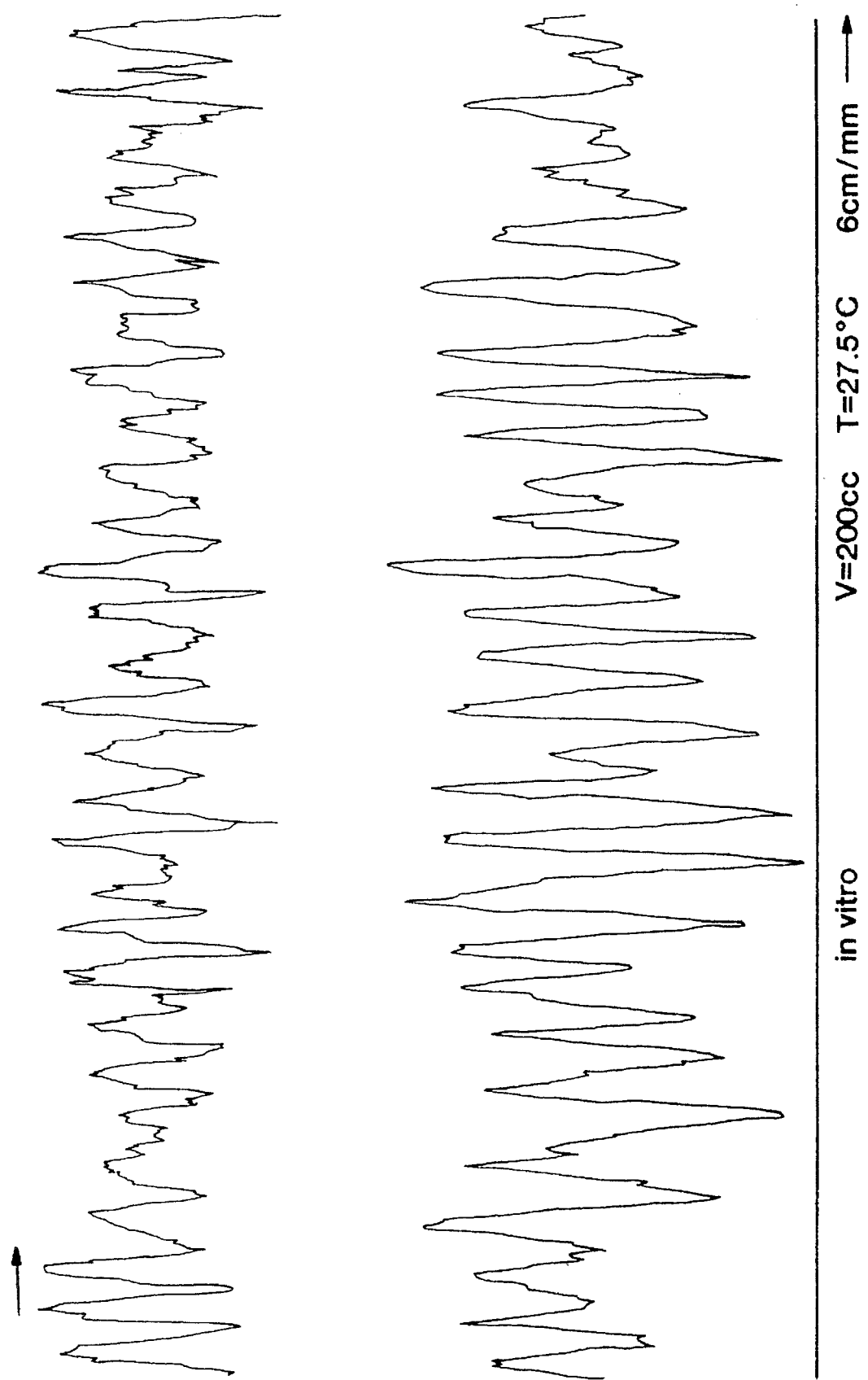
FIG. 15C  in vitro  V=200cc  T=27.5°C  6cm/mm

APPARATUS FOR EXAMINING THE FUNCTIONING OF BODY STRUCTURES COMPRISING SMOOTH MUSCLE WALLS

BACKGROUND OF THE INVENTION

1. Field of the Invention

The present invention is directed to a method for confirming patient's complaints as manifestations of a physiological condition. More particularly, the present invention is directed to a urodynamic technique for confirming a patient's complaint with respect to the bladder (e.g., urge or cramp) as a manifestation of a physiological condition; and apparatus for effecting such methodology.

2. Description of the Prior Art

In clinical cystometry, intraluminal pressure is recorded in relation to bladder volume (Griffiths, D. J., et al., "Detrusor Instability In Children", Neurourol. Urodyn. 1, 187–192 (1982); Abrams, P., "Detrusor Instability And Bladder Outlet Obstruction", Neurourol. Urodyn., 4, 317–328 (1985); Coolsaet, B. L. R. A., "Bladder Compliance And Detrusor Activity During The Collection Phase", Neurourol. Urodyn., 4, 263–273 (1985)). Often, spontaneous phasic and tonic variations in intraluminal pressure are observed (International Continence Society: Fourth Report On The Standardization Of Terminology Of Lower Urinary Tract Function, J. Urol., 53, 333 (1980)). It was noticed that the spontaneous variation in detrusor pressure in the normal human bladder did not occur until a relatively high volume was obtained (Plum, F., "Autonomous Urinary Bladder Activity In Normal Man", Neurol. 2, 497–503 (1960)); and it was hypothesized that the onset of the micturition reflex was triggered by these spontaneous contractions via afferent stimuli (Plum, F., et al., "The Genesis Of Vesical Rhythmicity", A.M.A. Archives of Neurology, Vol. 2, 487–496 (1960)). A certain amount of spontaneous variation in pressure, sometimes expressed as an "instability index": is assumed to be related to symptoms of urge (Murray, K., et al., "The Effect Of Opioid Blockade On Idiopathic Detrusor Instability", Proc. 12th Ann. Meeting, Leiden, 85–87 (1982)). In particular, when large spontaneous phasic pressure waves are seen during cystometry (e.g., larger than 15 cm $H_2O$), urge is labelled as motor urge. The spontaneous activity observed in situ is supposed to be neurogenic (Griffiths, D. J., et al., "Urinary Bladder Function And Its Control In Healthy Females" Am. J. Physiol., 251, R225–230 (1986)). Hence, the spontaneous activity observed in vivo (bladder instability) is supposed to have an origin other than that of the spontaneous activity observed in vitro.

A recent model, based on observations on total pig bladders in vitro and on observations in patients, suggests the spontaneous activity seen in vitro is normally neurally inhibited in vivo and may become manifest in cases of disturbed neural control (Coolsaet, B. L. R. A., et al., "New Concepts In Relation To Urge And Detrusor Activity" Neurourol Urodyn., 12, 463–471 (1993); Van Duyl, W. A., et al., "Evocation Of Unstable Detrusor Contractions By Stretch", Submitted to Eur. J. Urology (1994); Van OsBossagh, P., et al., "Filling State Of Bladder And Bladder Wall Activity: A Functional Model", Submitted To Neurourol. Urodyn. (1994)).

Conventionally, the main interest of urodynamic research has been to find techniques to confirm the patient's complaint of urge in terms of pressure. The causal relation between urge symptoms and detrusor over-activity has been clinically evaluated in several studies. To increase the chance of verification of the patient's complaint in terms of bladder pressure, ambulatory urodynamics (Waalwijk van Doorn, E. S. C., et al., "A Retrospective Study Of The Clinical Value Of Telemetric Urodynamics Compared With Standard Urodynamics In Patients With Urinary Incontinence", Biotelemetry IX, 159–160, H. P. Kimmich and M. R. Newman, Eds. (1987)) and provocative tests (Coolsaet, B. L. R. A., et al., "Detrusor Overactivity", Neurourol. Urodyn., 5, 435–447 (1988)) are performed. Despite these improved techniques, there is a poor correlation between detrusor pressure and clinical symptoms (Jorgensen, L., et al., "Vaginal Repair In Female Motor Urge Incontinence", Eur. Urol, 13, 2, 382 (1978)). The poor correlation between detrusor pressure and urge might be explained by the fact that detrusor pressure is an incomplete reflection of relevant phenomena in the bladder wall.

The concept of micromotion refers to the phenomenon of distributed spontaneous contraction activity in smooth muscle, particularly, of the urinary bladder (Van Duyl W. A., "Spontaneous Contractions In Urinary Bladder Smooth Muscle: Preliminary Results", Neurourol. Urodyn., 4, 301–308 (1985)). Several techniques have been published to measure minute displacements in tissue (Paolini, P. J., et al., "Dual diffractometer utilizing linear image sensor charge-coupled devices", Rev. Sci. Instr., 47, 698–702 (1976); and Roos, K. P., et al., "Individual Sarcomere Length Determinations From Isolated Cardiac Cells Using High Resolution Optical Microscopy And Digital Image Processing", Biophys. J., 40, 233–244 (1982)). To study (micro-) displacements in striated muscle, use can be made of the structure (sarcomeres) as landmarks for reference (Drake, A. D., et al., "A Fiber Fizeau Interferometer For Measuring Minute Biological Displacements", I.E.E.E. Trans. Biomed. Eng., BME-31, No 7, 507–511(1984)). Because smooth muscle lacks such a structure for reference, it is necessary to use markers to measure the (distribution of) micromotion in a strip. The displacement of such markers can be measured by means of a videotechnique (Hoffman, A., et al., "A Method For Measuring Strains In Soft Tissue", J. Biomech., Vol. 12, No. 10, 795–800 (1984)).

Micromotion patterns were observed in studies, in vitro, on strips of pig bladder tissue. As markers, light spots realized by thin optical fibers stuck through the tissue, were utilized; the local excursions being observed by means of the displacement of the fibertips. The fibertips could be followed by a video system, however, to analyze the motions, it was preferred to use a position-sensitive planar semi-conductor. By means of this technique, micromotions were observed with a resolution of approximately 50 µm (Van Duyl, W. A., "Spontaneous Contractions In Urinary Bladder Smooth Muscle: Preliminary Results", Neurourol. Urodyn., 4, 301–308 (1985); and Van Duyl, W. A., et al., "A Fiber Technique To Measure Patterns Of Micromotion In Strips Of Tissue" (In Preparation (1994)).

In the literature, many authors have reported spontaneous contractions observed, in vitro, as variations of force across a strip of smooth muscle (e.g., Levin, R. B., et al., "Relevance Of Spontaneous Activity To Urinary Bladder Function: An In Vitro And An In Vivo Study", J. Urol., 136, 514–521 (1986)) It has been shown that these spontaneous contractions of strips of the bladder (rabbit bladder) are different for longitudinal and transverse strips taken from the lower-, mid- and upper-part of the bladder (Potjer, R. M., et al., "Frequency Of Spontaneous Contractions In Longitudinal And Transverse Bladder Strips", Am. J. Physiol., 257, R781–R787 (1989)).

However, most authors take the spontaneous activity as an artifact and, hence, do not consider it to be physiologically relevant for in situ situations. Some authors mention the possibility of using the observation of spontaneous activity for pharmacological studies, in vitro. Nonetheless, spontaneous activity, in vitro, is considered to be a myogenic artifact.

SUMMARY OF THE INVENTION

In our view, spontaneous activity may be characterized as distributed micromotion which, under isometric conditions, causes a force across a strip as a result of the pattern of micromotion. Furthermore, in contrast to the prior art mentioned above, we believe that micromotion is physiologically and pathophysiologically relevant for bladder behavior, in situ. In particular, we have stated that micromotion characterizes the condition of the bladder in the collection phase, which can be expressed in a variable along a bladder performance scale (Van Duyl, W. A., "A Model For Both The Passive And The Active Properties Of Urinary Bladder Tissues Related To Bladder Function", Neurourol. Urodyn., 4, 275–283 (1985)).

Observations of micromotion patterns in strips have shown that the force across a strip is not uniquely related to micromotion in the strip (Van Duyl, W. A., et al., "Synchronization Of Spontaneous Contraction Activity In Smooth Muscle Of Urinary Bladder", Neurourol. Urodyn., 9, 547–550 (1990)) and, even that, micromotion may exist while there is no variation observed in the force across the strip.

It is evident that variation in detrusor pressure is caused by contractions in the wall. We suppose that spontaneous variation in detrusor pressure is caused by contraction patterns which are similar to the distributed patterns of (micro- or macro-) motion observed in strips of bladder tissue. Extrapolating the conclusions drawn from observations on strips to total bladders, the variation in bladder pressure is not uniquely related to motion patterns in the wall and there may be spontaneous micromotion which is not observed as a variation in pressure. The extent to which micromotion is reflected in variations in detrusor pressure depends on the amount of synchronized activity and the compliance of the bladder. Consequently, the condition of the bladder, expressed in terms of micromotion patterns in the wall, cannot be reliably judged from detrusor pressure.

Further micromotion may stimulate receptors in the bladder wall so that micromotion is the source of afferent neural activity. This activity informs the central nervous system about the condition of the bladder. Accordingly, micromotion may be the origin of the sensation of the filling state of the bladder, eventually leading to the desire to void or leading to the sensation of urge. Thus, micromotion is a fundamental phenomenon in relation to the pathology of urge. Accordingly, detrusor pressure clinically is less significant than micromotion in the detrusor wall. Moreover, it has been shown the pressure is only a rough, indirect and unreliable measure of micromotion patterns. In other words, there is a fundamental reason to give priority to develop techniques to measure micromotion instead of improving diagnostic techniques based on detrusor pressure.

Accordingly, the present invention provides a method for determining whether a body structure of a patient comprising a muscular wall member is functioning normally or abnormally, the method comprising:

(i) measuring the micromotion of the muscular wall member;

(ii) generating a parameter characteristic of the state of the body structure based on the measured micromotion; and (iii) comparing the parameter with a predetermined performance scale to determine whether the body structure is experiencing normal or abnormal function.

in another aspect, the present invention provides an apparatus for measuring the micromotion of the wall of a hollow organ, comprising:

a catheter having a first end and a second end;

an inflatable balloon disposed over the first end of the catheter, the inflatable balloon being fluid tightly sealed to said catheter at a position intermediate the first and second ends;

at least four electrodes affixed to an inner surface of the balloon, the at least four electrodes being spaced apart from one another when the inflatable balloon is at least partially inflated;

a respective electrically conductive lead electrically connected to each of the at least four electrodes, each respective electrically conductive lead having an electrically insulative covering thereover, each respective electrically conductive lead passing through the catheter and extending beyond the second end thereof.

BRIEF DESCRIPTION OF THE DRAWINGS

FIG. 2 illustrates a probe, as contemplated by the present invention, in place in the bladder of a patient.

FIG. 3A is a detailed illustration of an electrode mounted on the wall of the balloon, as contemplated by the present inventors.

FIG. 3B illustrates a technique for achieving the mounting of the electrode on the wall of the balloon, as illustrated in FIG. 3A.

FIG. 4 illustrates a probe, as contemplated by the present invention, prior to mounting of the inflatable balloon thereon.

FIG. 7 illustrates a construction of an electrode support for the presently contemplated probe to facilitate passage through the urethra.

FIGS. 8A, 8B and 9 illustrate alternative methods of mounting electrodes on the wall of the balloon.

FIGS. 15A, 15B, 15C and 15D illustrate plots of pressure and distance signals taken at varying filling volumes (100 ml, 200 ml, 300 ml and again at 100 ml) during in vitro testing of Bladder No. 8.

DETAILED DESCRIPTION OF THE INVENTION

The concept of micromotion refers to the phenomenon of distributed spontaneous contraction activity in smooth muscle. Such micromotion has now been determined to be physiologically and pathophysiologically relevant for body structures containing smooth muscle wall members. In fact, such micromotion may characterize the condition of such body structures (which may include the urinary bladder, blood vessels, the fallopian tubes, the intestines, the uterus, the cervix, the stomach, the urethra, and the antrum).

Thus, there has now been developed a method for determining whether a body structure of a patient comprising a muscular wall member formed of smooth muscle tissue is functioning normally or abnormally. The method comprises: (i) measuring the micromotion of the muscular wall member; (ii) generating a parameter characteristic of the state of the body structure based on the measured micromotion; and (iii) comparing the parameter with a predetermined performance scale to determine whether the body structure is experiencing normal or abnormal function.

In its simplest form, such a method could involve merely determining over a period of time whether micromotion is taking place and/or the amplitude of such micromotion and comparing this data with a time record of patient complaints, e.g., cramps, pain, urge (sensation) etc. If no correlation with patient complaints were apparent, this would be indicative of a possible psychological, rather than a physiological, basis for the complaint.

Alternatively, more complex methods could involve the generation of an empirical performance scale. In such a method, the performance scale would be empirically determined by (a) measuring the micromotion of the muscular wall member of the body structure in a plurality of individuals known to have normal function of the body structure; (b) generating a value of a parameter based on the measured micromotion of step (a) characteristic of the state of the body structure for each of the plurality of individuals in step (a); (c) determining a range of the values of the parameter characteristic of the state of the body structure indicative of normal function of the body structure; (d) measuring the micromotion of the muscular wall member of the body structure in a plurality of individuals known to have abnormal function of the body structure; (e) generating a value of a parameter based on the measured micromotion of step (d) characteristic of the state of the body structure for each of the plurality of individuals in step (d); and (f) determining a range of the values of the parameter characteristic of the state of the body structure indicative of abnormal function of the body structure.

The parameter which characterizes the state of the body structure could be a directly determinable one, such as amplitude or frequency of micromotion, or a more complex parameter that characterizes micromotion (or patterns thereof) in terms of stochastic non-linear dynamics (chaos-theory).

Figure 1:
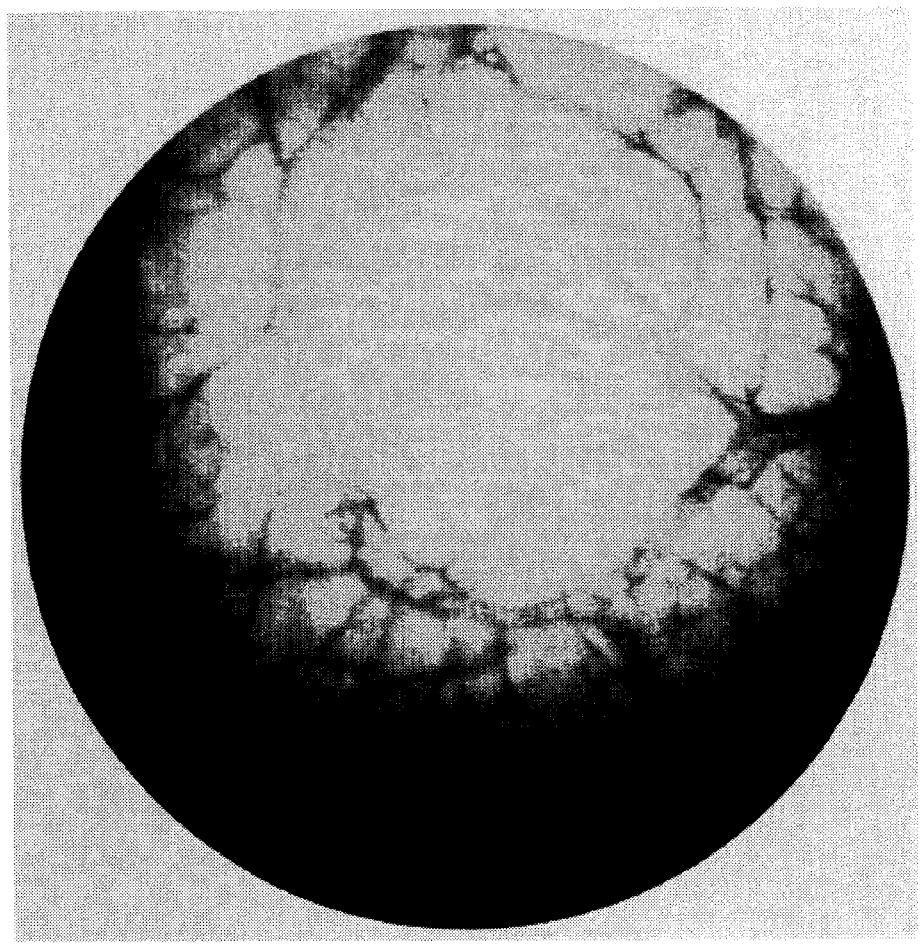
FIG. 1 is an endoscopic picture of the wall of a bladder showing the pattern of blood vessels therein.

The actual measurement of micromotion of the muscular wall member may be effected by attaching at least one detectable marker to the muscular wall member and detecting motion of the at least one detectable marker. Detection of the marker could be visual, e.g., small balls of albumin injected into a surface layer of the wall, or spots of Evans-blue painted on the wall whose movement could then be monitored by a camera (endoscopically) with a videoregistration system. (Alternatively, the detectable marker could be a blood vessel within the wall, as illustrated in FIG. 1, and motion of the blood vessel or a portion thereof could be visually tracked in the same manner as the aforementioned artificial markers.)

Detection of the marker could be magnetic in nature, e.g., by magnetic resonance imaging (MRI) where the marker contains an atomic nucleus having at least one proton or one neutron that is unpaired. Alternatively, the marker could be the inherent biomagnetic activity of the smooth muscle as measured by a SQUID (Superconducting Quantum Interference Device) magnetometer (see: Golzarian, J., et al., "First Biomagnetic Measurements Of Intestinal Basic Electrical Rhythms (BER) In Vivo Using A High-Resolution Magnetometer" Abstract, American Motility Society, Biennial Symposium, September 1992; Golzarian, J., et al., "Non-Contact Measurement Of Biomagnetic Signals In Ischemic Small Intestine, Abstract", Ass. for Ac. Surgery, 26th Annual Meeting, Montreal, November 1992; and Staton, D. J., et al., "First Magnetic Measurements Of Smooth Muscle In Vitro Using A High Resolution DC-SQUID-Magnetometer", IEEE Eng. Med. and Biol. Soc., 113, 2 (1991).)

Detection of the marker could be via a RADAR technique, wherein the marker was reflective of electromagnetic radiation in the radio frequency range.

Alternatively, in the larger hollow organs having a muscular wall, e.g., the bladder, the intestines, the uterus, the cervix, etc., a displacement transducer could be sutured to the muscle wall to measure local contractions.

A further technique involves the utilization of at least two detectable markers attached to the muscular wall member, the markers being spaced apart from one another, and detecting relative motion between the at least two detectable markers. Such relative motion could be detected by the techniques previously discussed.

The presently preferred technique for measuring micromotion involves the utilization of such a two marker system and it will be described hereinafter, along with a novel apparatus for effecting the technique.

In particular, the presently preferred technique is based on the measurement of electrical resistance between points on the muscular wall and will be described in terms of its applicability to measurements on the muscular wall of hollow organs, especially the urinary bladder.

As shown in FIGS. 2 and 4 a filling catheter 1 is surrounded by a thin-walled elastic balloon 3, which may be formed from latex rubber (e.g., in the laboratory a condom was utilized as the balloon), which is fluid-tightly connected to the catheter 1 by a silicone ring 5.

The catheter with the deflated balloon attached thereto is brought into the lumen of the bladder via the urethra and the bladder is extended by filling the balloon with a liquid having a predetermined electrical resistivity, e.g., a salt solution such as 0.9% NaCl. Small disks of silver 7 (diameter of about 3 mm and thickness of about 1 mm) are used as the electrodes 9. Each disk 7 is provided with a small knob 11 (diameter of about 3 mm), as best seen in FIG. 3A. The electrode is fixed to the wall of the balloon 3 by means of a rubber ring 13. As shown in FIG. 3B, the electrode may be mounted to the balloon wall 3 by pressing the small 11 knob into the open end of a small tube 12 with the balloon wall intermediate the small knob and the tube; a rubber ring 13 from a supply of expanded rubber rings disposed about the small tube may then be slipped off the small tube (as shown by the arrows) so as to contract about the small knob and thereby affix the same to the wall of the balloon. In this way, an array of four electrodes are fixed to the wall of the balloon. In the bladder, when the balloon 3 is filled with a liquid, then the wall of the balloon is pressed against the wall of the bladder 15; and the small knob 11 on each electrode 9 is pressed into the wall of the bladder so that the position of the electrode relative to its location in the bladder wall is fixed. In this regard, it is crucial that the elasticity of the thin-walled balloon is such that the local motion of the bladder is not hindered and is followed by the electrodes.

FIG. 4 shows the probe (without the balloon 3 mounted thereon) comprising the catheter 1 and four electrodes 9 with the insulated leads 17 for each of the electrodes passing through the channel of the catheter, a flexible connection member 19, a Y-connector 21 and a liquid-tight seal 23 in one of the legs of the Y-connector. The channel of the catheter 1 is also used for filling the balloon by virtue of a liquid supply line 25 connected to the other leg of the Y-connector 21. The liquid supply line 25 may also be used to measure the intra-luminal pressure of the bladder, when the balloon is inflated and a manometer (or other pressure gauge) is connected thereto.

Using the aforementioned apparatus, a contraction or dilation of the bladder tissue between two electrodes is transformed into a variation of the distance between these electrodes. Because the electrodes are in contact with the electrically conductive liquid (saline) filling the balloon, this variation of distance can be measured as a variation of the electrical resistance between the electrodes. The interpretation of resistance in terms of distance is based on a separate in vitro calibration of the probe.

In order to avoid polarization of the electrodes and electrolysis of the solution filling the balloon, the resistance is measured by use of an AC-current of 10 kHz. To account for various safety regulations, the supplied current is approximately 10 µA. This means that the voltage to be measured between electrodes is in the range of µV's. For such low voltages, it is necessary to reduce the errors caused by the electrode/saline interfaces. For that reason, a four-points-measurement technique is utilized, using apparatus as illustrated in FIG. 5.

Figure 5:
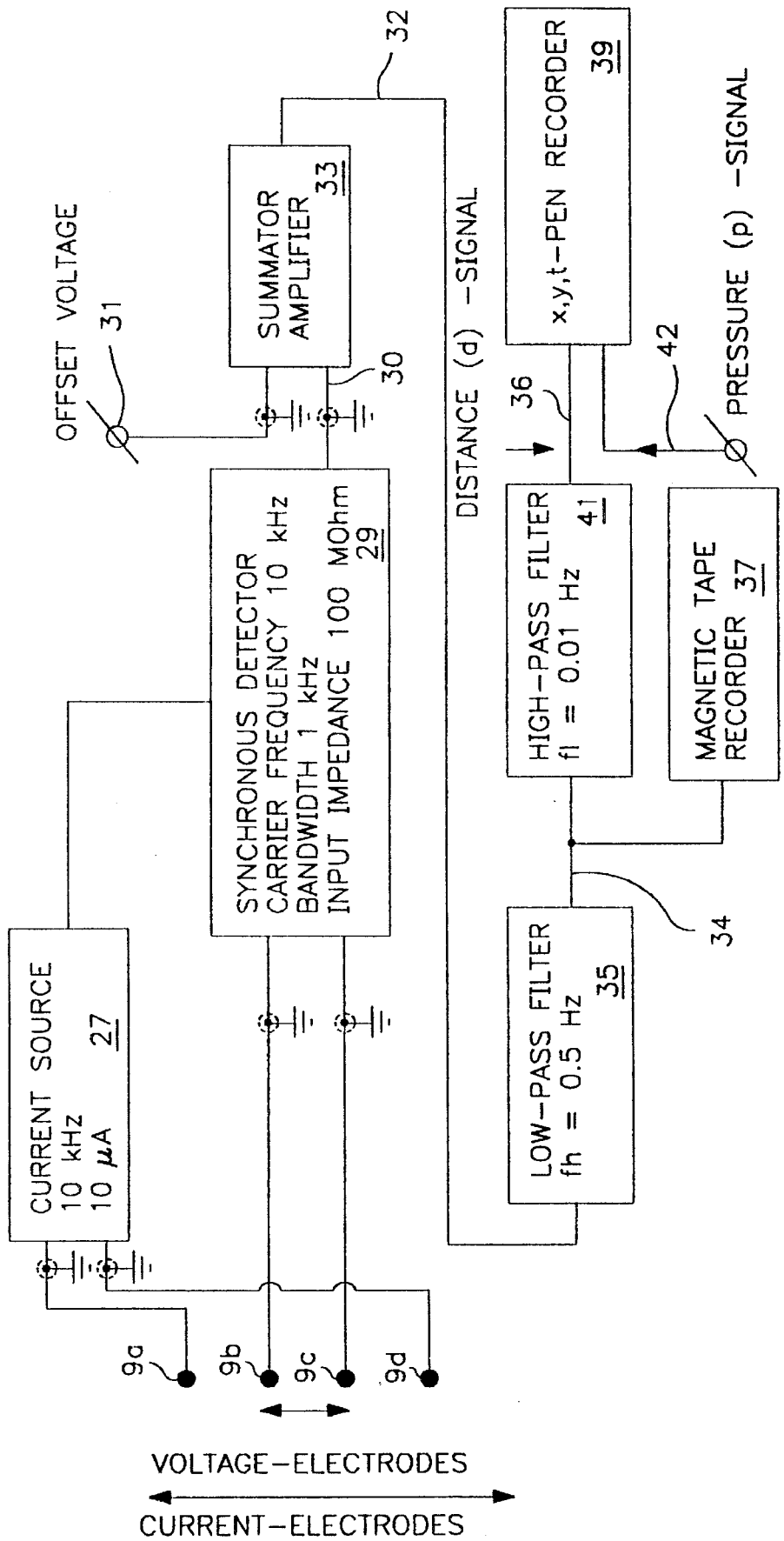
FIG. 5 is a schematic illustration of the apparatus used in the presently contemplated four-points-measurement technique.

As shown in FIG. 5, in the four-points-measurement technique, the current is applied from a power source 27 via an outer pair of electrodes 9a, 9d of an array of four, referred to as the current-electrodes, while the voltage is measured between an inner pair of electrodes 9b, 9c, referred to as the voltage-electrodes. The voltage is amplitude-modulated by the variation in the distance between the voltage-electrodes and to a lesser extent by the variation in the distance between the current-electrodes.

By applying a demodulation technique with synchronous detection, with compensation for phase shift (lock-in amplifier 29: bandwith around 10 kHz is 1 kHz, input impedance of 100M Ohm) a voltage is obtained which varies according to the amplitude of the 10 kHz AC-voltage with a sufficiently high signal-to-noise ratio.

In order to study the variation in distance between the electrodes with high resolution, a constant value of the measured voltage is subtracted from the voltage signal 30 exiting lock-in amplifier 29 by feeding said voltage and an offset voltage 31 to summing amplifier 33. (This offset can be interpreted as a certain distance between the electrodes and can be chosen to correspond to the initial distance between the voltage-electrodes 9b, 9c.)

In order to reduce the contribution of bubbles of gas, in the metabolic bath, in in vitro experiments, to the motion signal, the voltage signal 32 exiting summing amplifier 33 is filtered through low-pass filter 35 (cut-off frequency of 0.5 Hz). This filtered signal 34 is recorded on a magnetic tape recorder 37. During experiments, only the phasic (small) variations in the voltage signal 36 are recorded with a pen recorder 39 by passing the filtered signal 34 through a high-pass filter 41 (cut-off frequency of 0.01 Hz) prior to recording.

The intra-luminal pressure signal 42 (obtained by means not shown but well-known in themselves) is also simultaneously recorded by the pen recorder 39.

The measurements are performed under isovolumetric conditions so that variations of the positions of the electrodes are caused solely by the small spontaneous local motions in the bladder wall. Because micromotion is distributed all over the bladder wall, not only the positions of (distance between) the voltage-electrodes vary, but also the positions of the current-electrodes. This means that the variation of the voltage between the voltage-electrodes is not a direct measure of the variation in the distance between these electrodes, but needs to be corrected for contributions caused by variation of the positions of the current-electrodes.

This effect has been studied during calibration of the equipment. The system was calibrated for a symmetrical arrangement of the array of four electrodes. When the distance between the voltage-electrodes is d and the distance between the current-electrodes is D, then a variation δD contributes to a variation in voltage between the voltage-electrodes, which can be erroneously interpreted as a variation of the distance between the voltage-electrodes equal to δd ("crosstalk"). The "crosstalk" is estimated (first order approximation) to amount to $$\delta d = f \delta D \qquad (1)$$

where "f" is the "crosstalk"-factor, which is estimated to amount to $$f = d/D \qquad (2).$$

This means that this "crosstalk"-factor is smaller when the ratio between the distance (d) between the voltage electrodes and the distance (D) between the current-electrodes is smaller. When calibrating the apparatus with values of D=45 mm and d=5 mm, the sensitivity was 10 μV per mm variation in d. A variation (δD) of the distance (D) between the current-electrodes produced a variation of the voltage between the voltage electrodes that corresponded to a variation (δd) of the distance (d) between the voltage-electrodes such that $$\delta d = 0.15 \, \delta D.$$

When the balloon has isotropic elastic properties, the ratio of d/D is independent of the volume of the balloon, so that the error estimated by equation (1), as a first order approximation, is independent of volume. However, the geometry of the current distribution in the solution may cause deviations from the estimated error which will depend on volume. These non-linear aspects have not been studied in detail.

As an alternative to the electrical resistance measuring technique, visible markers could be fixed to the inside wall of the balloon. In this embodiment, the micromotions of the wall could be tracked via endoscopic techniques combined with video-registration. (However, due to the non-immobilized position of the endoscope, it may be necessary to view more than two markers at any given time in order to compensate for gross motions.)

Figure 6A:
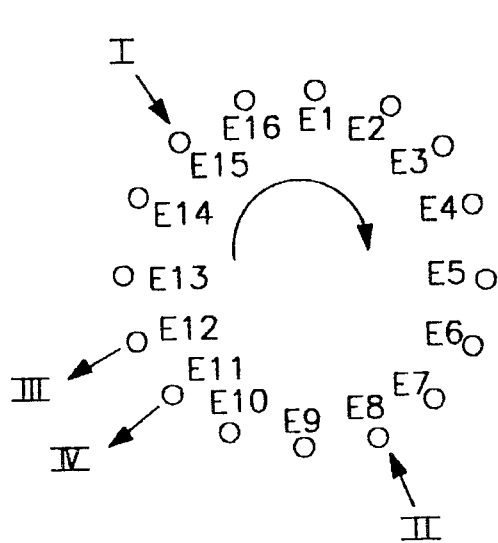
FIGS. 6A and 6B illustrate two successive positions in the switching sequence of a 16-electrode array using the four-points-measurement technique.
Figure 6B:
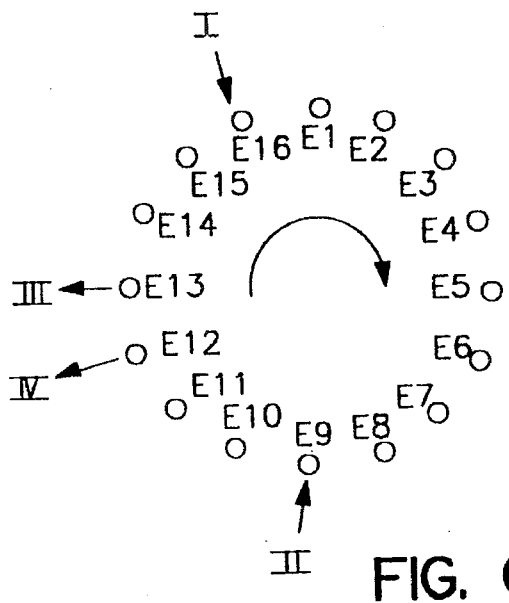
Figure 6C:
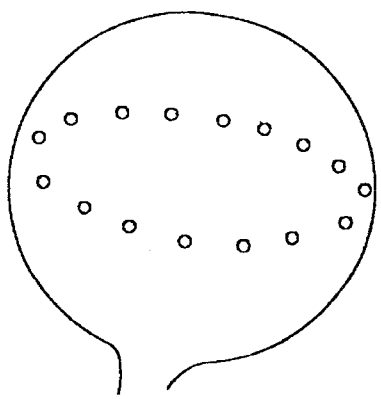
FIG. 6C illustrates a radial orientation of the 16-electrode array relative to the catheter.
Figure 6D:
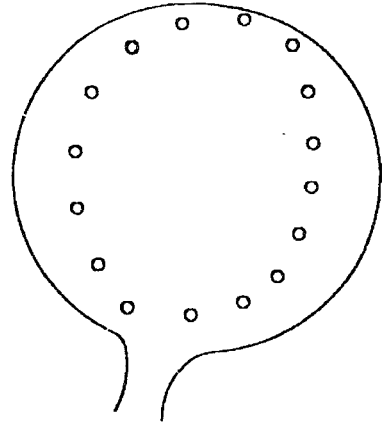
FIG. 6D illustrates a longitudinal orientation of the 16-electrode array relative to the catheter.

In any event, in order to investigate the heterogeneity of motions, a system utilizing multiple markers (i.e., more than 2, e.g., 4, 6, 8, 10, 12, 14, 16, 18, 20, 22, 24, etc.) is required in order to detect motions at a plurality of locations on the bladder wall. A system based on sixteen electrodes as illustrated in FIGS. 6A, 6B and 6D is utilized.

An important limitation to the use of such a multi-electrode system in patients concerns the catheter, i.e., the diameter of the catheter needs to be as small as possible to pass the urethra without problems. For that reason, the initial positions of the electrodes on the wall of the balloon are chosen longitudinal to the catheter as shown in FIG. 6D because if placed radially as in FIG. 6C, the electrodes need to be arranged in a circle around the catheter which makes the probe too thick. To facilitate passing of the urethra, a small flexible strip 43 mounted at the end of the catheter 1 may be utilized as shown in FIG. 7. Holes 45 in the strip 43 can hold the electrodes 9 in their initial positions by a slightly lowered pressure (vacuum) in the balloon 3.

It is desirable that the initial diameter of the unstretched balloon is small so that foldings of the balloon around the catheter can be avoided and the electrodes are more easily held in their positions. Because there is a limit in stretching (approx. factor of 10) of the material of the balloon (latex), we need an initial unstretched diameter depending on the volume we want to reach, without the risk of damage of the balloon. Points of risk of damage, of course, are at the locations of the electrodes.

The effect of electrical pathways through the bladder wall via the wall of the condom (resistive and capacitive) have been measured in vitro and concluded to be neglectable, with saline in and outside the balloon. However, electrical shunting could introduce a more serious error when the wall is overstretched. In order to obtain optimal geometry, and to account for the compliance of the balloon compared to the compliance of the bladder, balloons in two or more sizes may be utilized (e.g., one for volumes up to 300 ml and another for larger volumes).

For the four-electrode system, we simply used the same technique in patients as used in vitro, and we did not bother about the size of the electrodes. For the multi-electrode system, it is crucial to practice size conservation of the probe.

To prevent slip between the wall of the balloon and the bladder wall, use of electrodes with the small knobs has been adopted, as noted above. However, the disadvantage of the hard knobs is that they hinder the passage of the probe through the urethra and make the probe more vulnerable. Small grains, e.g., of latex, outside the balloon offer a good alternative.

In order to have a good transformation of motion in the wall to the electrode in a well defined location, the electrodes (or the uninsulated end of the lead) can be pricked in the grain of latex as is illustrated in FIGS. 8A and 8B. As shown in FIG. 8A, the electrode 9 actually pierces the wall of the balloon 3, but the wall of the balloon is sealed (and the electrode fixed in place) by curing a drop of latex 47 at the point of penetration, to form a small protuberance on the outside surface of the balloon. Alternatively, the bare end 17A of the lead 17 (the remainder 17B of which is covered by insulation) may actually pierce the wall of the balloon 3, but the wall of the balloon is sealed (and the bare end fixed in place with a portion of the bare end, e.g., a length of about 2 mm, exposed inside the balloon) by curing a drop of latex 47 at the point of penetration, to form a small protuberance, e.g., about 1.5 mm in diameter and about 2 mm high, on the outside surface of the balloon. By forming a small knot in the bare end of the lead which is outside the balloon, the lead is securely fixed in place upon curing the latex. Also, from the electrical point of view, this technique is superior since it avoids interfaces of different metals (e.g., silver electrode/ steel lead).

Figure 9:
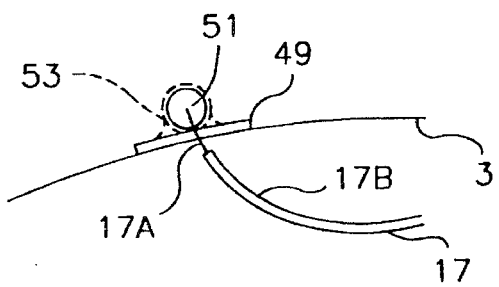

Alternatively, as shown in FIG. 9, a small disc of latex 49, for local reinforcement, is glued to the wall of the balloon 3. An uninsulated portion 17A of the lead 17 is pricked through the wall of the balloon and through the disc. At the tip of the uninsulated portion 17A a small ball of solder 51 prevents withdrawal of the lead. Then the ball is covered with a thin layer 53 of latex to electrically insulate the ball. A small part of the uninsulated portion 17A remains exposed outside the balloon, and hence functions as the electrode, while the remainder 17B of the lead 17 is covered with insulation. This technique also results in a considerable space saving.

The use of 16 electrodes has the problem of passing so many leads through the lumen of the catheter. The number of leads could be reduced by using a multiplexing microswitch situated at the end of the catheter. Such microswitches are available (Medtronic, Maastricht, The Netherlands).

Figure 10:
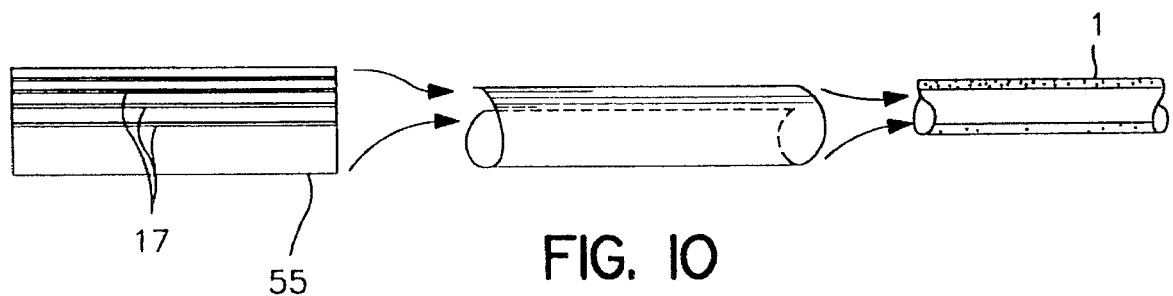
FIG. 10 illustrates the use of printed leads to conserve space within the catheter.

Alternatively, in order to save space in the lumen of the catheter, a thin plastic sheet 55 with the leads 17 printed on it can be rolled up and brought inside the catheter 1 as shown by the arrows in FIG. 10.

Figure 11:
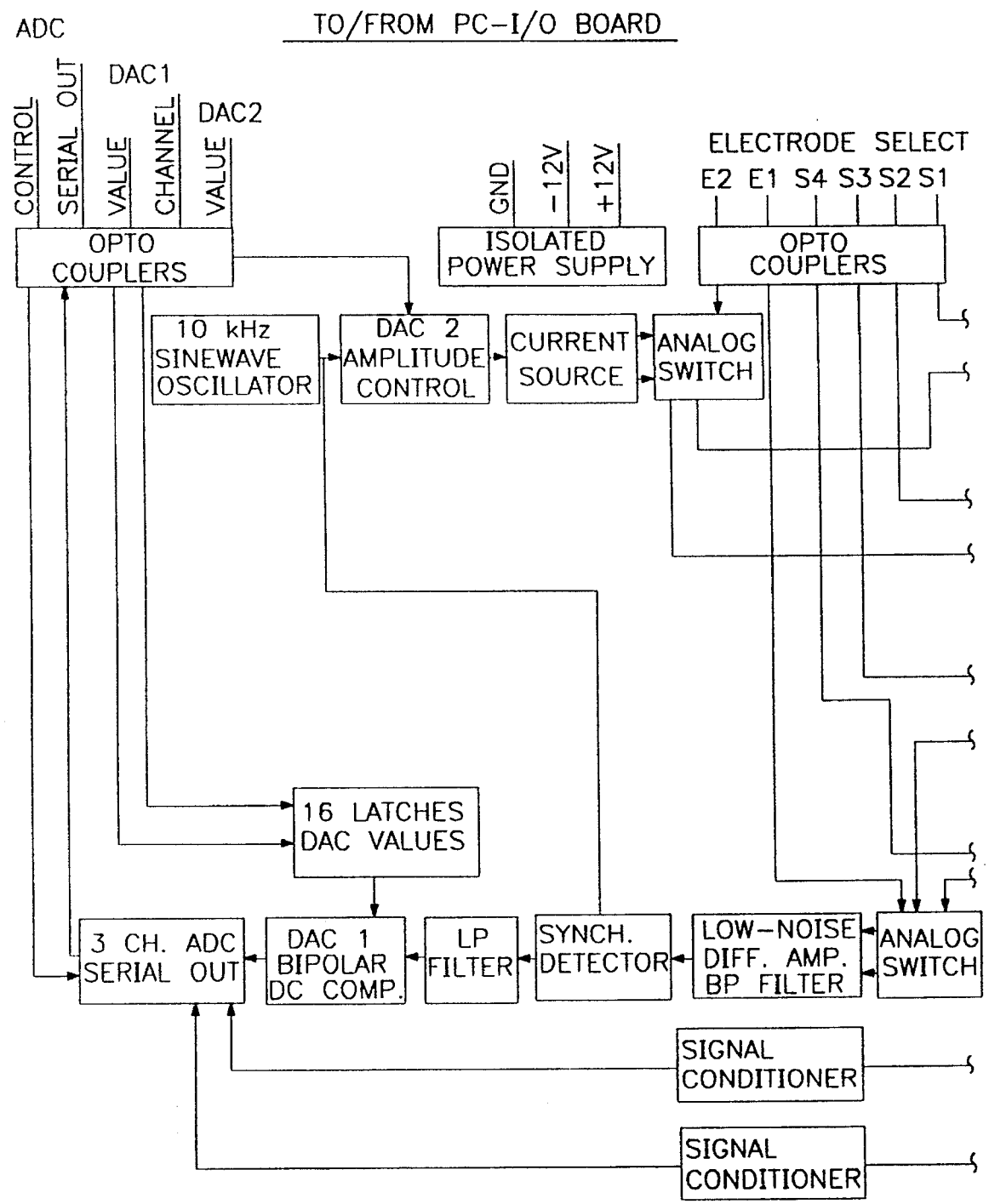
FIG. 11 illustrates a schematic block diagram of the apparatus for utilizing the 16-electrode array of the present invention.
Figure 11B:
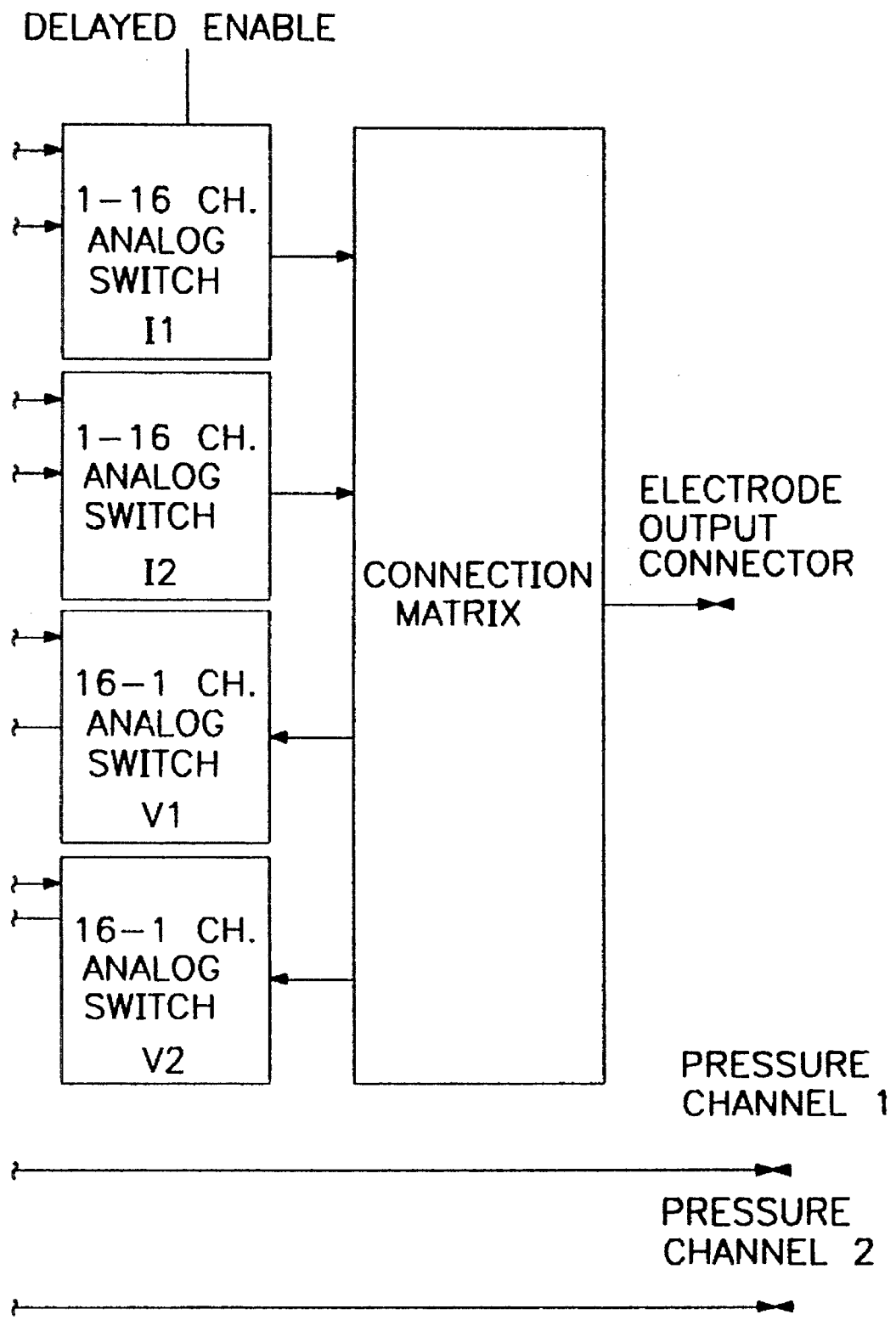

FIG. 11 illustrates the block diagram of the electronics to be used in combination with a probe with 16 electrodes. We need an AC current as a carrier that does not have the risk of stimulating muscles or neurons. According to the I.E.C.-601-1 regulations on electrical safety, a maximum AC current of 100 μA, 10kHz is allowed to be used. (We use an AC-current of 10 μA, 10kHz.) The electronics is placed in a closed box (safe to water and without knobs) which is connected to the probe via a short flat cable (connection matrix). According to a switching sequence, as illustrated in FIGS. 6A and 6B, four electrodes of the array of 16 electrodes (E1–E16) are switched to be used for a 4-points measurement as has been validated in the previous studies: the outer pair (I, II) are switched (I1,I2) to a current source, the inner pair (III, IV) are switched (Vl,V2) to a differential amplifier. By synchronous detection and band-pass-filtering, a voltage is obtained that is a measure of the distance between the electrodes which at that time are switched to be the voltage-electrodes.

An offset value of the voltage, chosen via a PC, is subtracted via a DAC. The output is connected to a 12 bit ADC, which can be fed as serial digital data to the PC.

The device is intended to sample a maximum of 16 electrodes and two pressure channels (bladder and abdominal pressure) at a maximum sampling rate of 5 per second. Such a high sampling rate is needed in order to use this technique, and also to measure the distribution of contractions in case of an activated bladder.

The multi-electrode system offers the possibility to correct the motion signals partly for "crosstalk" from the variation in the distance between the current-electrodes to the voltage between the voltage-electrodes.

With the circular arrangement of 16 electrodes, there are 16 intervals, denoted by d1 ... d16.

Let us denote by dn' the measured voltage across interval dn, with n=1 ... d16. The current-electrodes are chosen symmetrically around the voltage-electrodes with a distance in vitro. Moreover, this simple correction procedure can be done on-line by computer.

EXAMPLES

In-Vitro Testing

The micromotion detection technique, based on 4-electrodes as described above, has been applied to measure spontaneous activity on total pig bladders in-vitro. The bladders were obtained from pigs sacrificed for cardiovacular research.

The fresh total pig bladder with partly intact urethra was suspended in a metabolic solution (Krebs solution at 37° C., bubbled with 95% $O_2$ 5%. The probe (catheter with condom and 4-electrodes (FIGS. 2 and 4) was introduced in the bladder lumen via the urethra, which was subsequently sutured around the catheter. Then the bladder was allowed to equilibrate for 30minutes. Subsequently, the balloon in the bladder was filled via the catheter by means of a syringe with saline solution at approximately 37.5° C. to a certain volume (e.g., 100, 200, 300 ml). At a constant volume, detrusor pressure and micromotion in the wall were recorded during periods of, e.g., 10–20 minutes. Values of some parameters, which are roughly estimated from the recordings, are shown in Table 1.

TABLE 1

| BLADDER NO. | V [ml] | T [C.] | Ap [cm $H_2O$] | Tp [s] | Ad [mm] | Td [s] | Te [h] | COMMENTS |
| --- | --- | --- | --- | --- | --- | --- | --- | --- |
| 1 | 200 | 37.8 | 0.8 | 10 | 1.0 | 10 | 1 | |
| 2 | 200 | 37.6 | 2.0 | 40 | 0.5 | 30 | 1 | |
| 3 | 200 | 37.0 | 10. | 25 | 2.0 | 25 | 1.5 | |
| 4 | 200 | 37.0 | 15. | 40 | 1.0 | 20 | 1.5 | |
| 5 | | 150 | 37.8 | 0.1 | 45 | 0.1 | 45 | |
| 6 | | 200 | 37.6 | 1.0 | 15 | 0.1 | 15 | |
| 7 | 150 | 37.4 | 0.2 | | 0.1 | | | effect |
| | | 38.6 | | | | | | of T on |
| | | 37.6 | | | | | | activity |
| 8 | 100 | 37.6 | | | | | | effect |
| | 200 | 37.5 | | | | | | of V on |
| | 300 | 37.5 | | | | | | activity |
| | 100 | 37.5 | | | | | | |

V = filled volume of the bladder (ml)
T = temperature of the bath (°C.)
Ap = order of magnitude of the amplitude of pressure (p-) waves (cm $H_2O$)
Tp = order of magnitude of duration of pressure (p-) waves (s)
Ad = order of magnitude of the amplitude of variation in distance (distance (d-) waves) (mm)
Td = order of magnitude of duration of distance (d-) waves (s)
Te = duration of time elapsed previous to the shown recording (hr)

D. The distance D may be chosen to enclose, e.g., 5 intervals, so that approximately D=5d. Let us denote by Dn the distance between the current-electrodes around the nth interval d between the voltage electrodes. This means that:

$$Dn = dn-2 + dn-1 + dn + dn+1 + dn+2 \quad (3)$$

Now $$dn' = dn + f \cdot \delta Dn \quad (4)$$

where f is the "crosstalk"-factor, see (2). Formula (4) can be used to derive a first order corrected value of dn, provided $\delta Dn$ and f are know.

$\delta Dn$ can be estimated as the change of the length of enclosed intervals determined in the previous two sample cycles, corrected for "crosstalk" in previous cycles. The "crosstalk"-factor can be obtained from calibration studies, As can be seen in the recordings discussed hereinafter, often a pressure (p-) wave coincides with a distance (d-) or motion wave, but not always and not always in the same phase. At some places in the shown recordings, (dis-)similarities in the variation in pressure with the variation in motion have been marked. Situations where a wave is seen in pressure or motion while it is lacking in a wave in motion or pressure, respectively, are marked in the recordings by "o". In situations where a contraction coincides with a pressure increase, or a dilatation coincides with pressure decrease, the waves are said to be in phase and this is marked by "+". Where motion waves and pressure waves are in anti-phase, this is marked by "−".

The distance signals are not corrected for "crosstalk". In each recording, the scale of the variation of distance and variation of pressure are given, which are derived from the calibration measurements.

Bladder No. 1

Figure 12A:
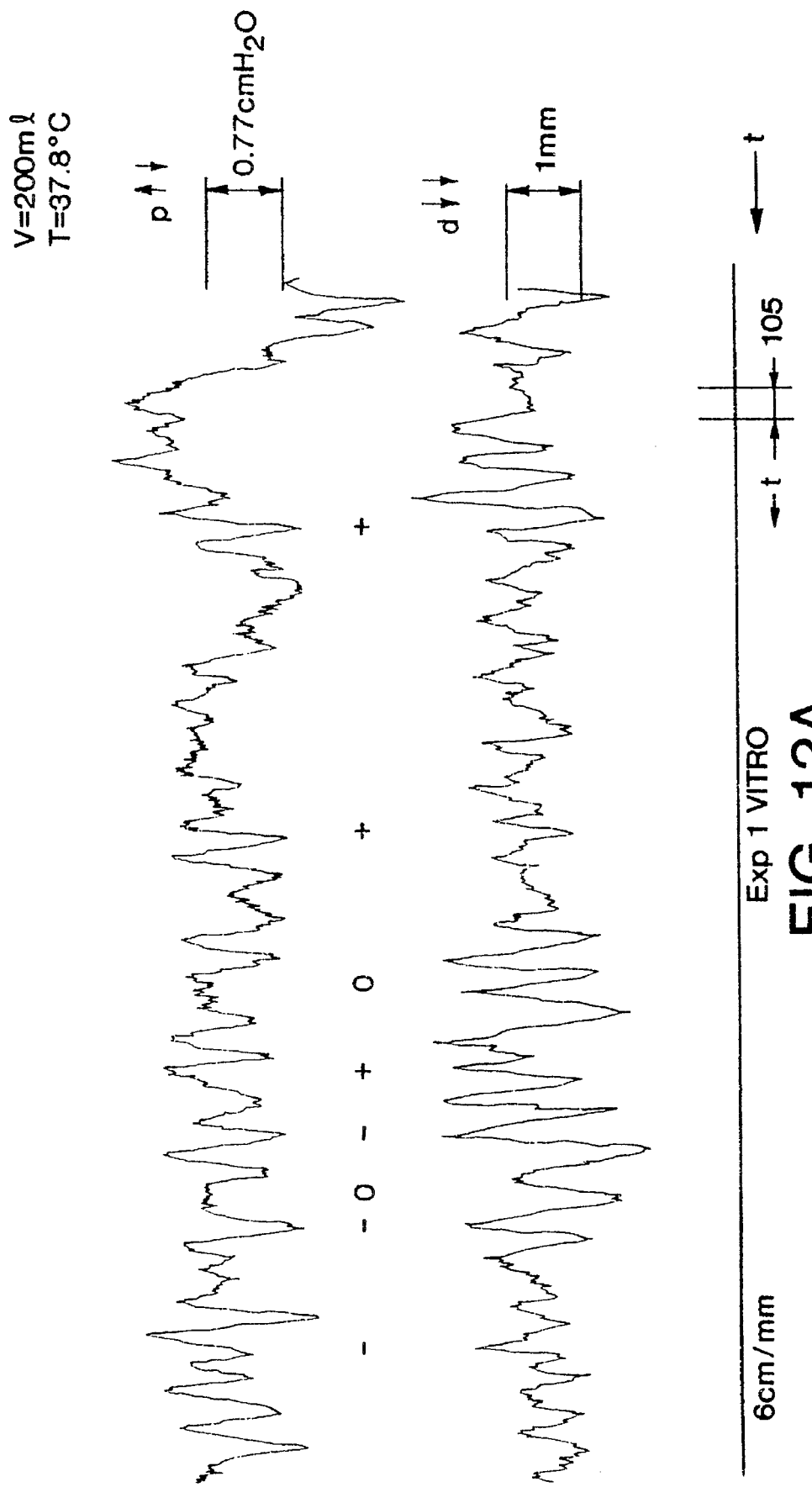
FIG. 12A is a plot of pressure and distance signals obtained during in vitro testing of Bladder No. 1.

As shown in FIG. 12A, the distance signal is rhythmic with an amplitude of approx. Ad=1 mm and a period of approx. Td=10 s. The pressure varies with an amplitude of Ap=0.8 cm $H_2O$, with approx. the same period as the distance, Tp=10 s. However, the pressure variation is not identical to the variation in distance between the voltage-electrodes. There are situations of in-phase and of anti-phase. This indicates that the pressure variation is not only determined by the contractions at the observed location of the bladder wall, but also by contractions at other locations.

Bladder No. 2

Figure 12B:
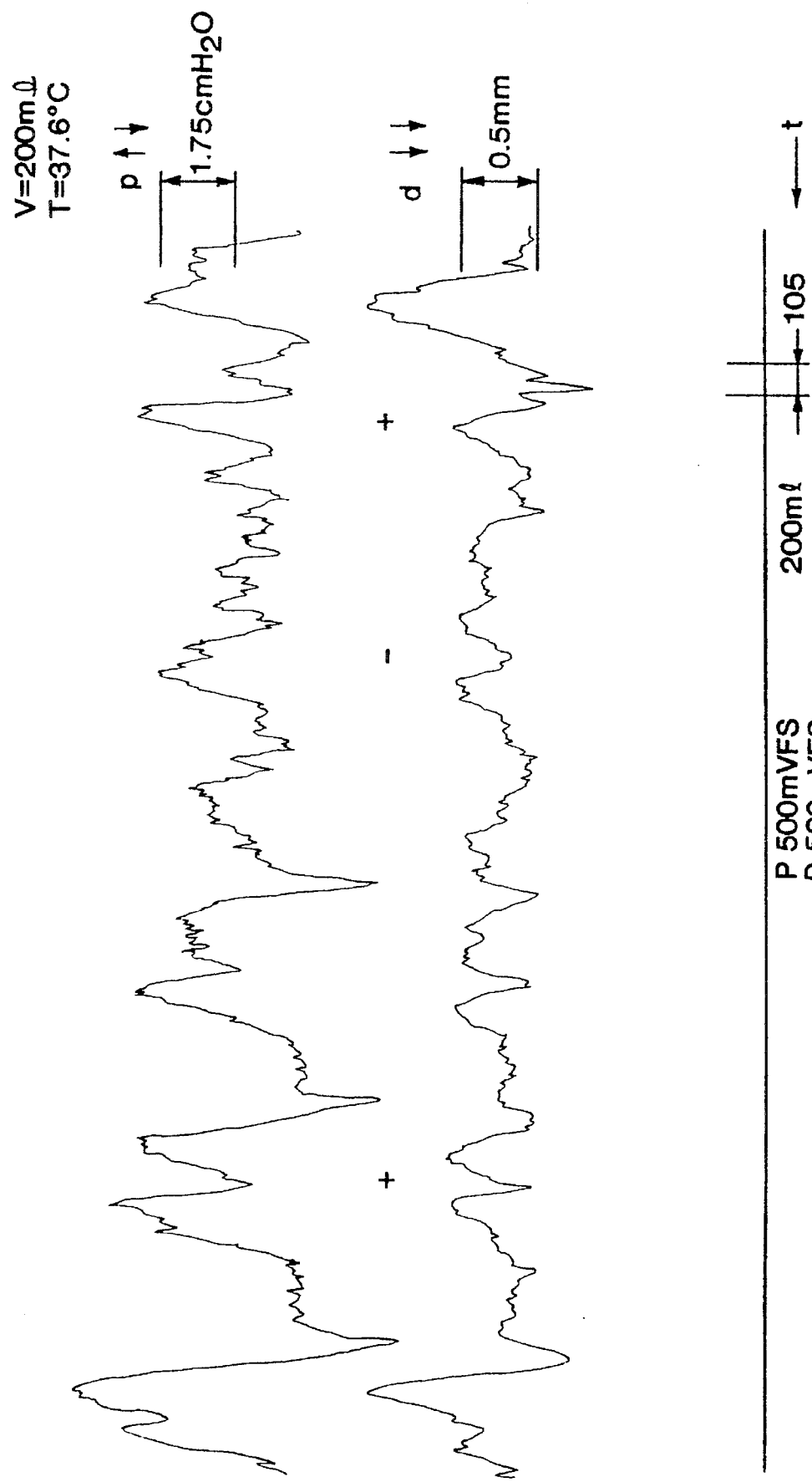
FIG. 12B is a plot of pressure and distance signals obtained during in vitro testing of Bladder No. 2.

As shown in FIG. 12B, compared to bladder no. 1, the waves have the same magnitude but are less pronounced; the frequency is significantly lower.

Bladder No. 3

Figure 12C:
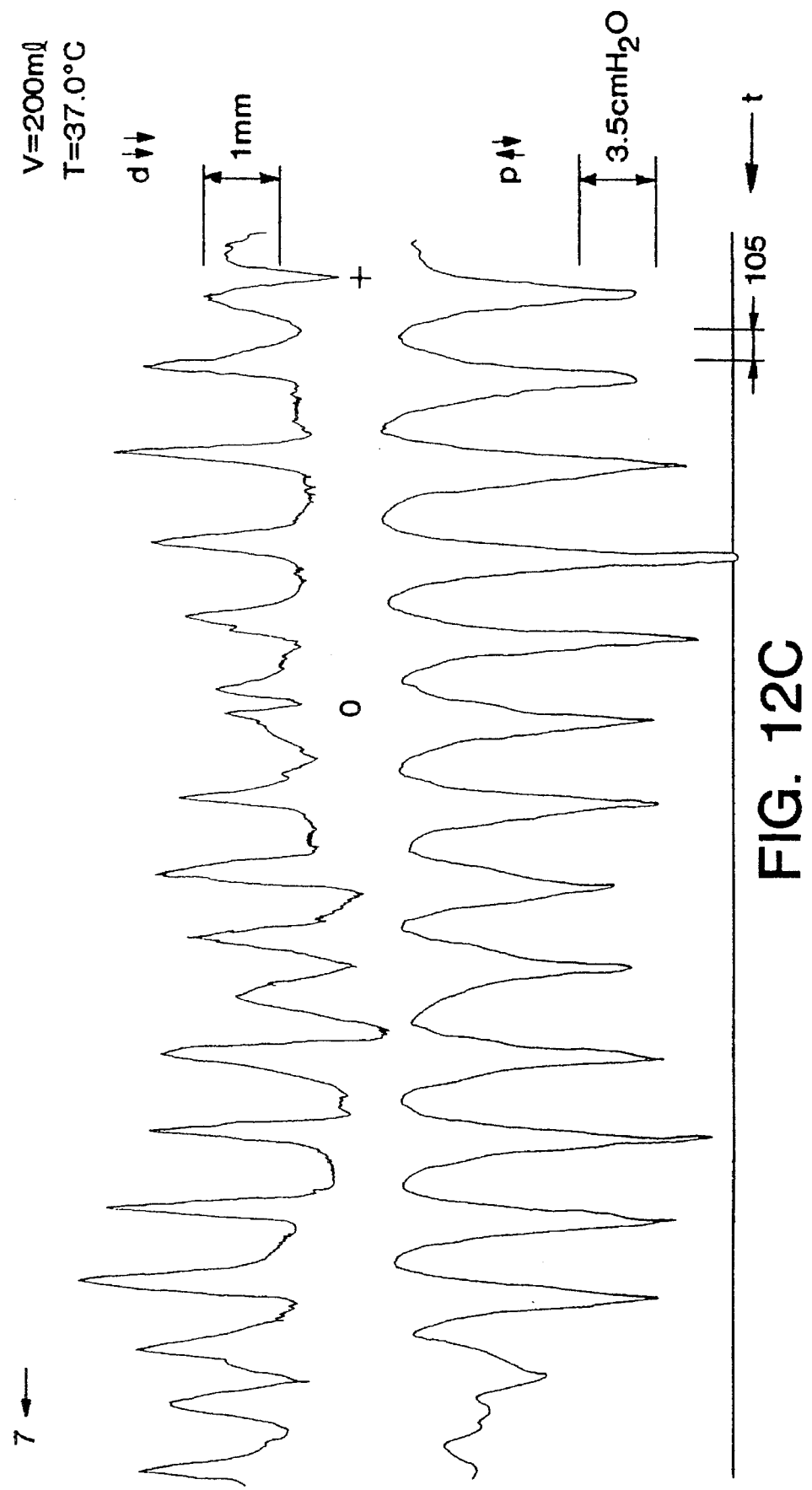
FIG. 12C is a plot of pressure and distance signals obtained during in vitro testing of Bladder No. 3.

As shown in FIG. 12C, distinct p- and d- waves are to be seen (Ap=10 cm $H_2O$, Tp=25 s, Ad=2 mm, Td=25 s.) and the p- and d-waves are rather synchronous but often in anti-phase.

Bladder No. 4

Figure 12D:
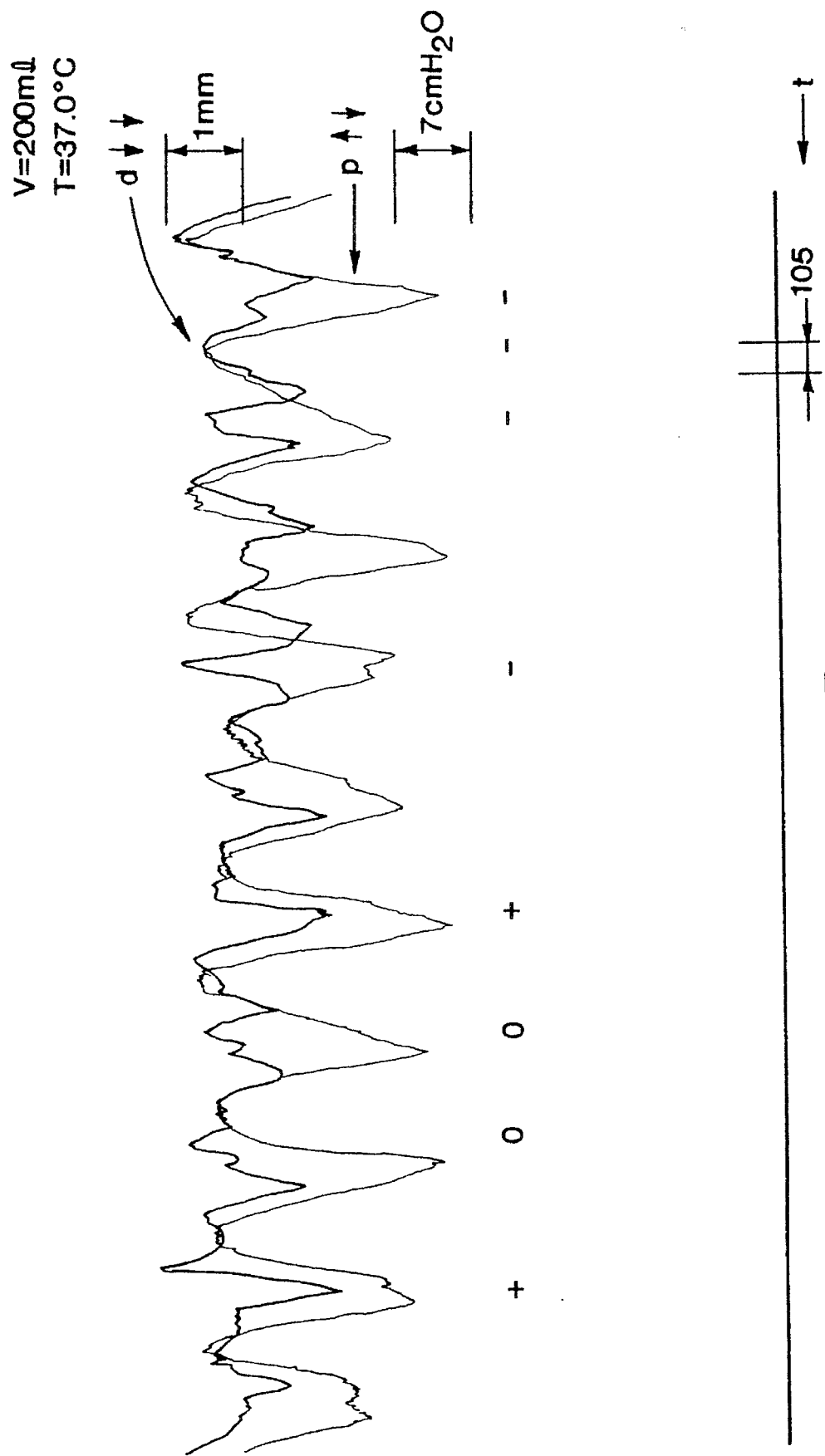
FIG. 12D is a plot of pressure and distance signals obtained during in vitro testing of Bladder No. 4.

As shown in FIG. 12D, distinct p- waves (Ap=15 cm $H_2O$, Tp=40 s.) and d- waves in phase and in anti-phase (Ad=1 mm, Td=20 s.) are to be found. The spontaneous phasic pressure waves are so large that, if it were observed in the bladder in situ, according to the I.C.S. criteria, this bladder should be classified as unstable and judged to cause motor urge. In other words, spontaneous contractions in vitro (supposed to be myogenic) can be in the same range as pathologic spontaneous contractions in situ (supposed to be neurogenic).

The distance signal shows small variations not to be seen in pressure. This demonstrates that the variation in distance has higher frequency components than the pressure.

Bladder No. 5

Figure 12E:
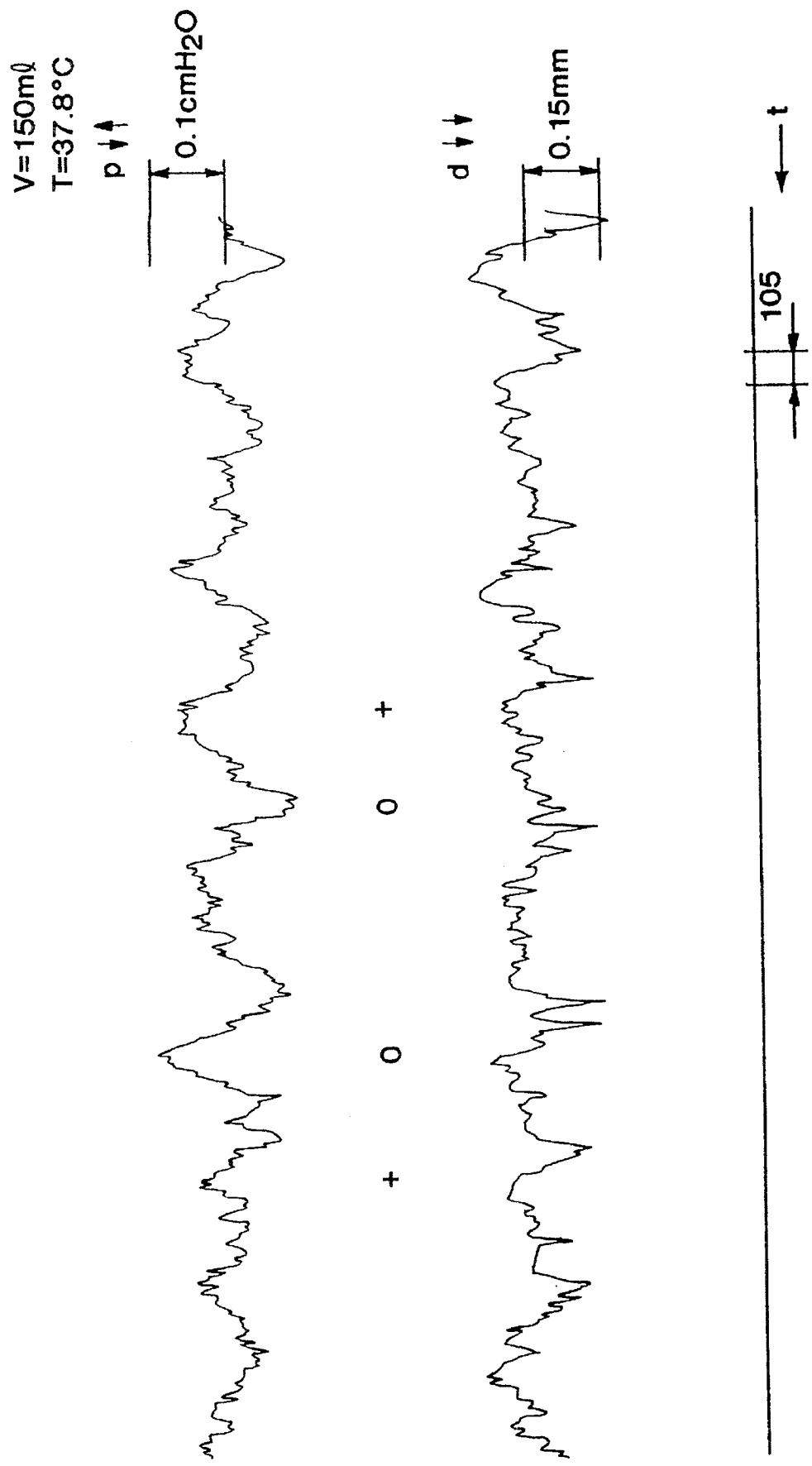
FIG. 12E is a plot of pressure and distance signals obtained during in vitro testing of Bladder No. 5.

As shown in FIG. 12E, with values of Ap=0.1 cm $H_2O$, Tp=45 s, Ad=0.1 mm and Td=45 s, this is an example of pressure waves and motions which are much smaller than in the previous cases.

Bladder No. 6

Figure 12F:
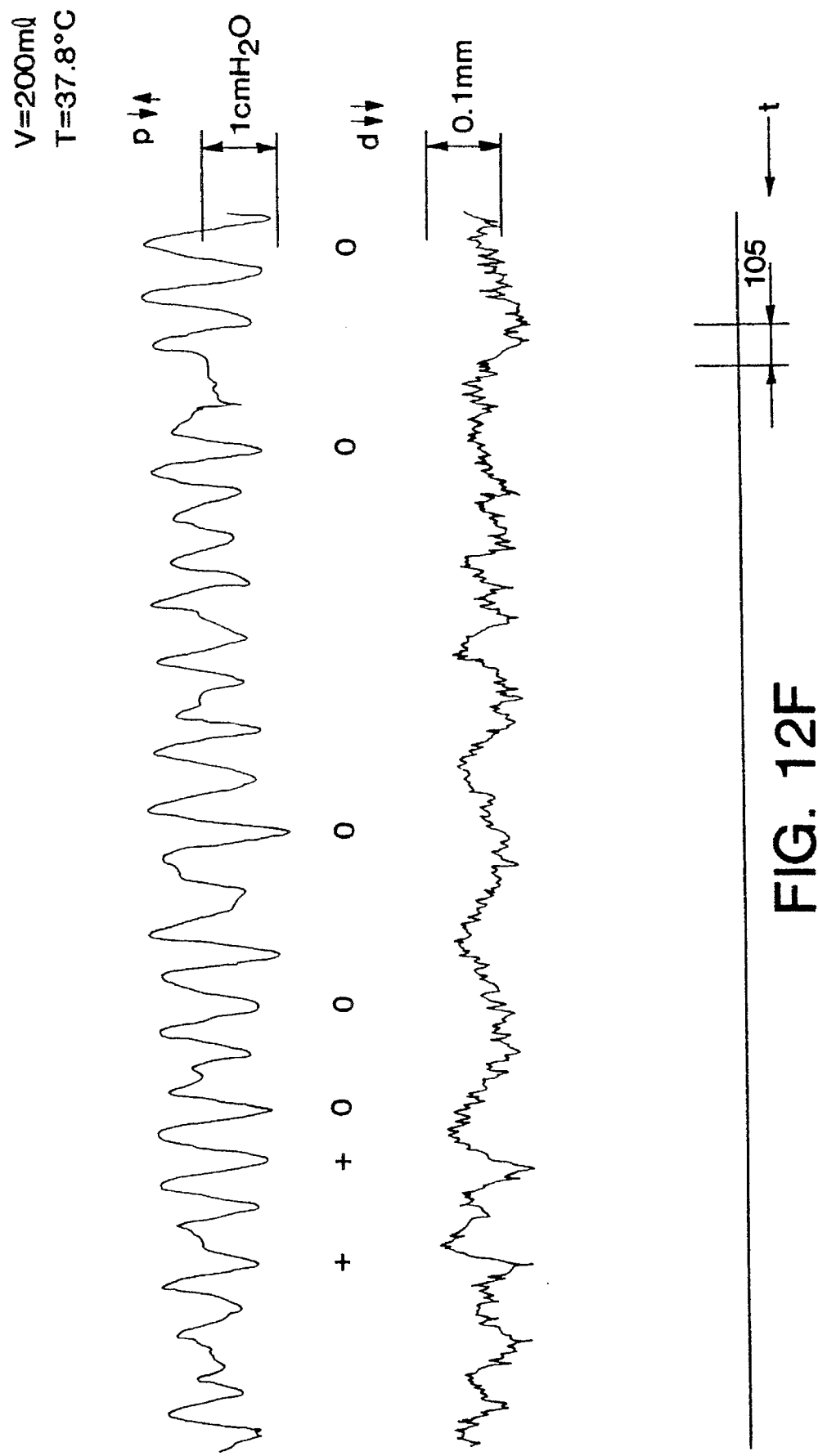
FIG. 12F is a plot of pressure and distance signals obtained during in vitro testing of Bladder No. 6.

As shown in FIG. 12F, with values of Ap=1 cm $H_2O$, Tp=15 s (distinct), Ad=0.1 mm and Td=15 s (not distinct), this is an example of small motions associated with normal pressure waves. Both signals are rather dissimilar. This recording demonstrates that the pressure waves are caused mainly by contractions in other regions of the bladder.

Bladder No. 7

Figure 13A:
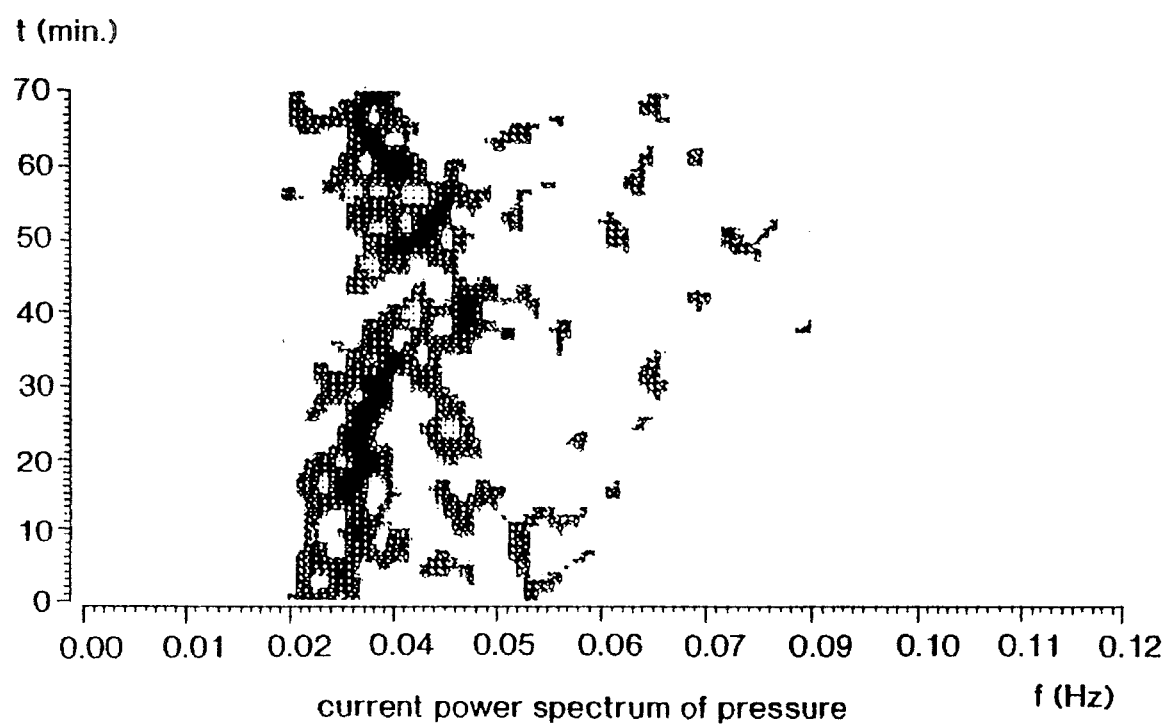
FIG. 13A is a power spectrum of the variation of pressure signals in response to changing temperature during in vitro testing of Bladder No. 7.
Figure 13B:
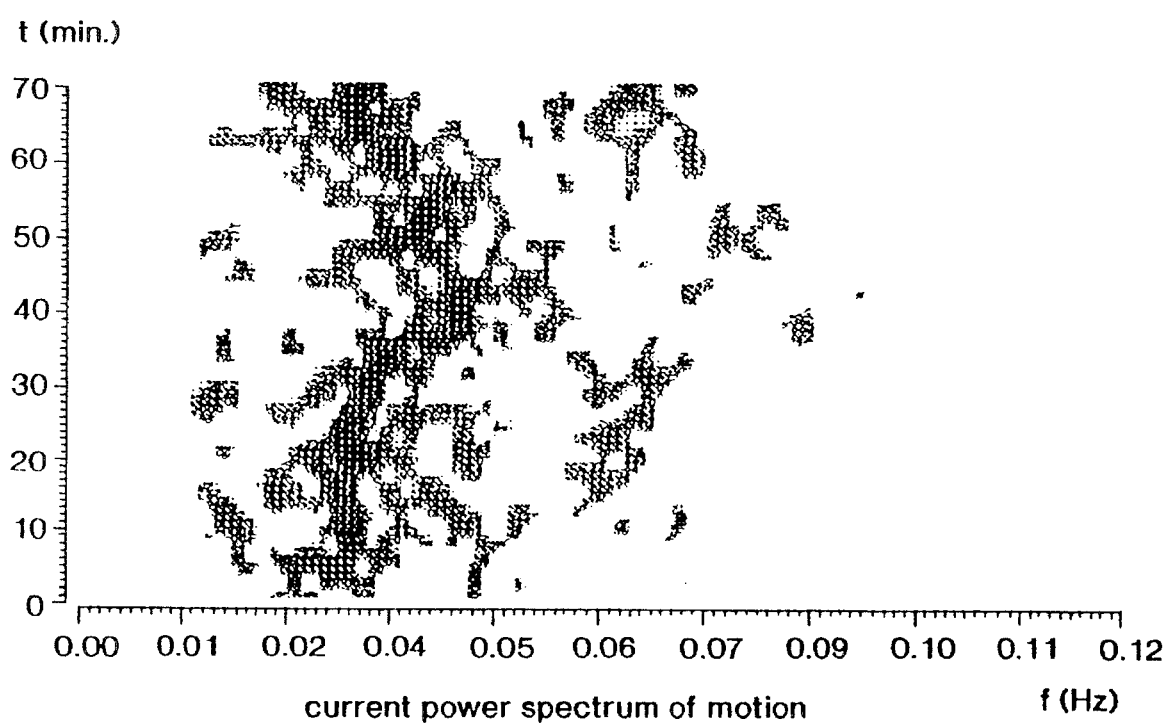
FIG. 13B is a power spectrum of the variation of distance signals in response to changing temperature during in vitro testing of Bladder No. 7.

This experiment was performed to investigate the effect of temperature on the spontaneous activity. T varied from 37.4 to 38.6and back to 37.6 C. The frequency spectra of the variations in the pressure and the distance are determined by calculating the fast-fourier-transform of successive overlapping episodes of the signals. Each episode concerns 256 s of recording, and the overlapping interval of successive episodes is 64 s. In this way, running spectra of the spontaneous variation in pressure and distance are obtained. These spectra are represented by means of a gray plot, as illustrated in FIGS. 13A and 13B. In the gray plot, the gray scale is a measure of the power of frequencies (f) during successive episodes (n). FIG. 13A concerns the power spectrum of the variation in pressure, and FIG. 13B concerns the power spectrum of the simultaneously recorded variation in distance. Both gray plots show broad frequency ranges, but both also show small black bands indicating that there is a dominating frequency. This dominating frequency is shifted to the right when temperature is higher, and returns to its original location when temperature is lowered again to its original value. The course of the dominating frequency in the spectra of the pressure and of the distance are similar. The broadness of the spectra of the d- signal is larger than that of the p- signal.

Figure 14:
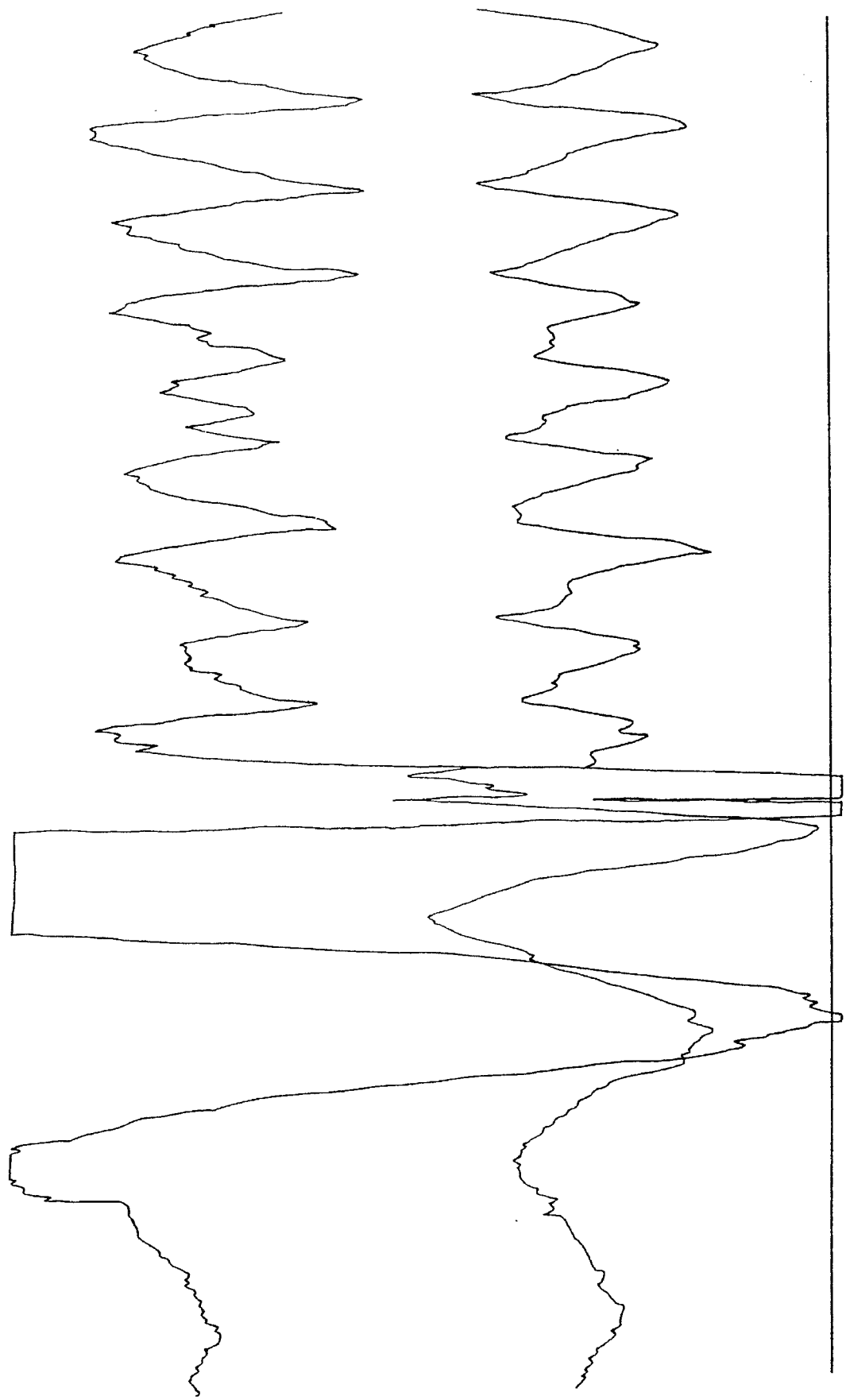
FIG. 14 illustrates the effect of adding acetylcholine to the metabolic bath during measurement of the pressure and distance signals in in vitro testing of Bladder No. 7.
Figure 15A:
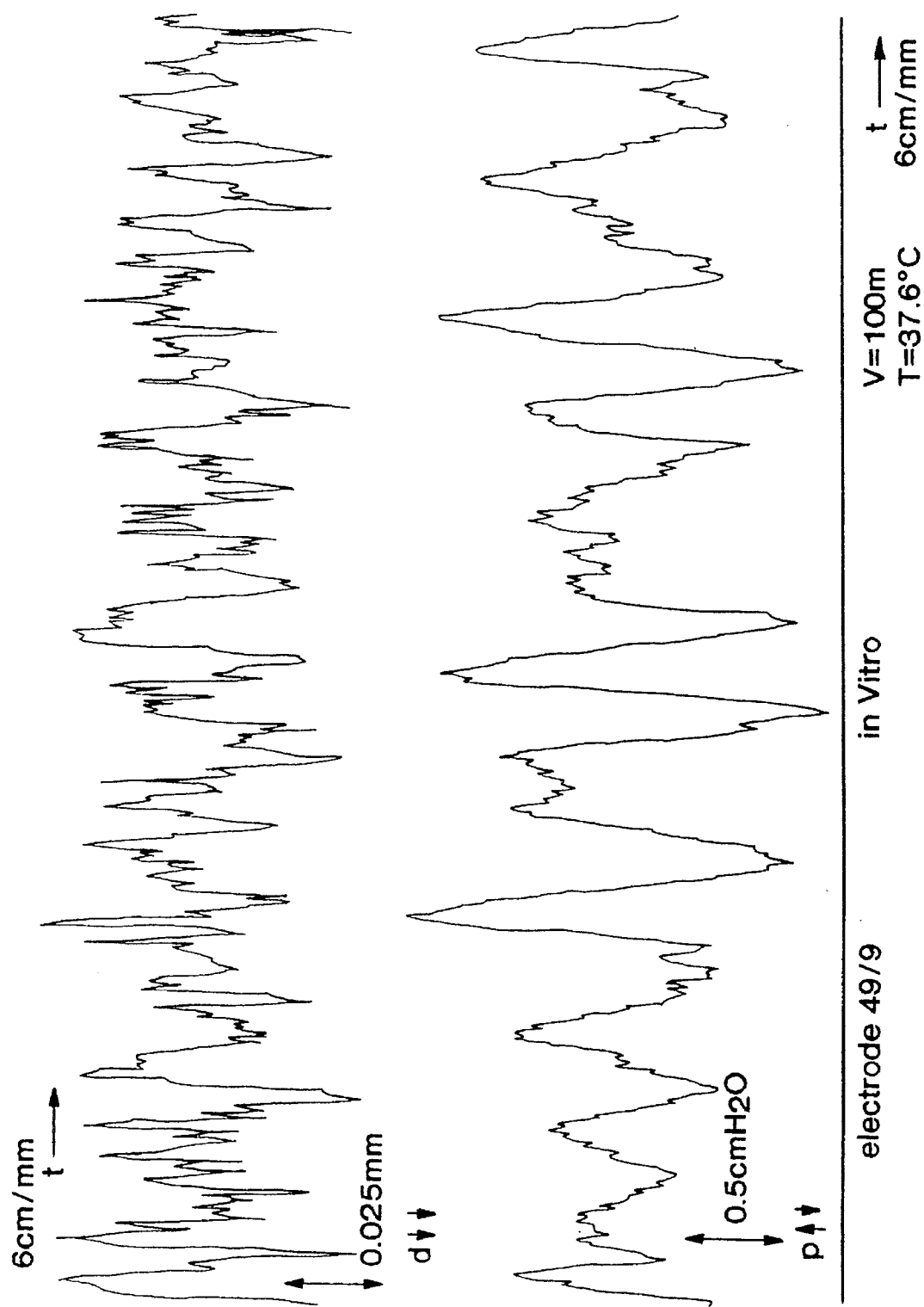
Figure 15B:
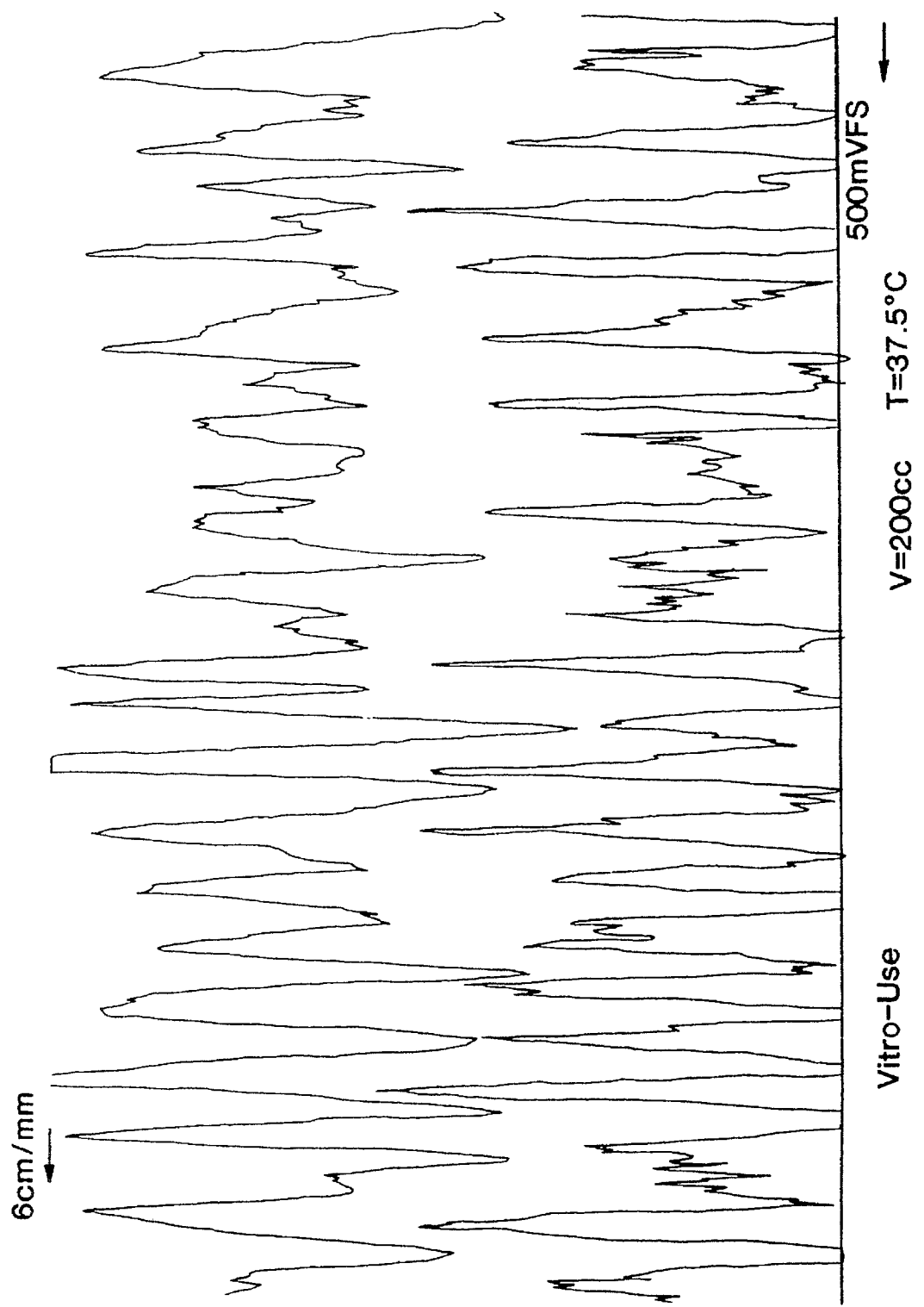
Figure 15D:
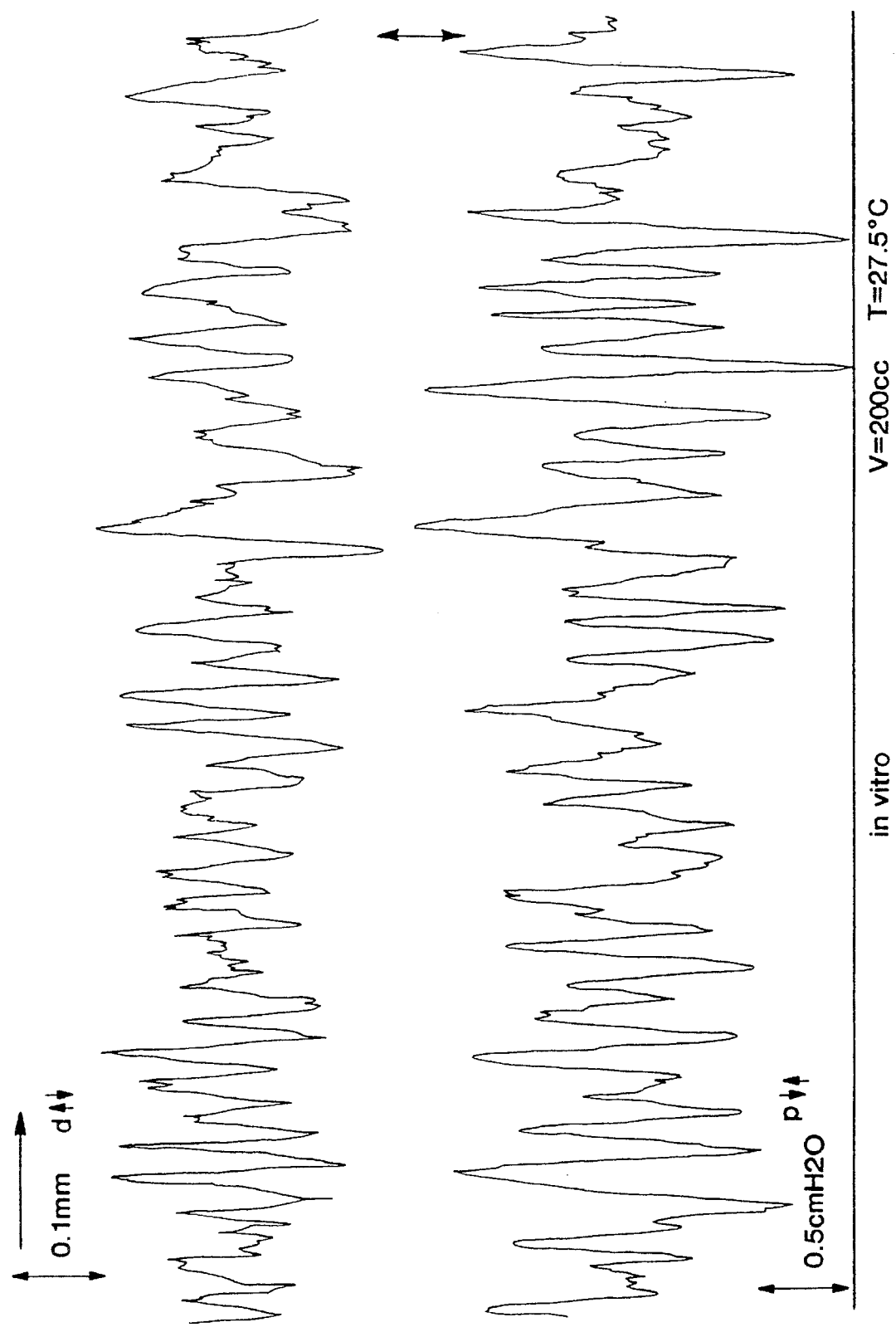

At the end of this experiment, we added a small amount of acetylcholine to the bath. The effect is shown in FIG. 14. The pharmacologically stimulated large waves in pressure and distance are synchronous, and in phase.

Bladder No. 8

An experiment was performed to find a relation between spontaneous activity and volume. The measurements were done at the following volumes: V=100 ml (T=37.6 C); V=200 ml (T=37.5 c); V=300 ml (T=37.5 C); and V=100 ml (T=37.5 C).

FIGS. 15A, 15B, 15C and 15D show parts of the recording of the experiment successive in time at different volumes: in 15A: V=100ml, in 15B: V=200 ml, in 15C: V=300 ml and in 15D: V=100 ml. The time recordings do not show a systematic relation between spontaneous activity and volume.

From the above, it can be stated that all of the pig bladders showed in vitro spontaneous activity with phasic variation in pressure in the range of 1–20 cm $H_2O$, and motions detected as variation in the distance between the electrode in the range of 0.1–10%. We never found (long) episodes with the bladder wall at rest. Generally, pressure varies not synchronously with distance. p- waves and d- waves coincide in phase or in anti-phase, or don't coincide at all. Generally, the frequency spectrum of motion is broader and has higher frequency components than the spectrum of pressure.

An important conclusion is that the variation in pressure is caused by motions in the wall, but in a complicated way; there are different islands of spontaneous activity in the wall. The pressure is not a unique reflection of phenomena in the wall. Increase in temperature causes a (reproducible) increase in the (dominating) frequency of the power spectrum of the variation in pressure and in motion.

In-Vivo Testing

For the patients, the same equipment and electrodes were used as for the in vitro studies. The patients were in a lithotomy position. The catheters were sterilized in cidex. Prior to the measurement, the bladder was emptied. The balloon was placed such that the electrodes were positioned at the dorsal side of the bladder wall. It is important to prevent bubbles of air in the lumen of the balloon, because that can affect the voltage between the electrodes seriously and in unknown degree. The positioning of the electrodes at the dorsal side reduces that risk. During the measurement, the urine in the bladder was drained via an extra catheter placed along the probe. Intraluminal and intra-abdominal pressure were recorded simultaneously with the motion in the wall. The electronic equipment was fed from the mains via an isolation transformer.

Patient No. 1 (Complaint: incontinence)

Figure 16:
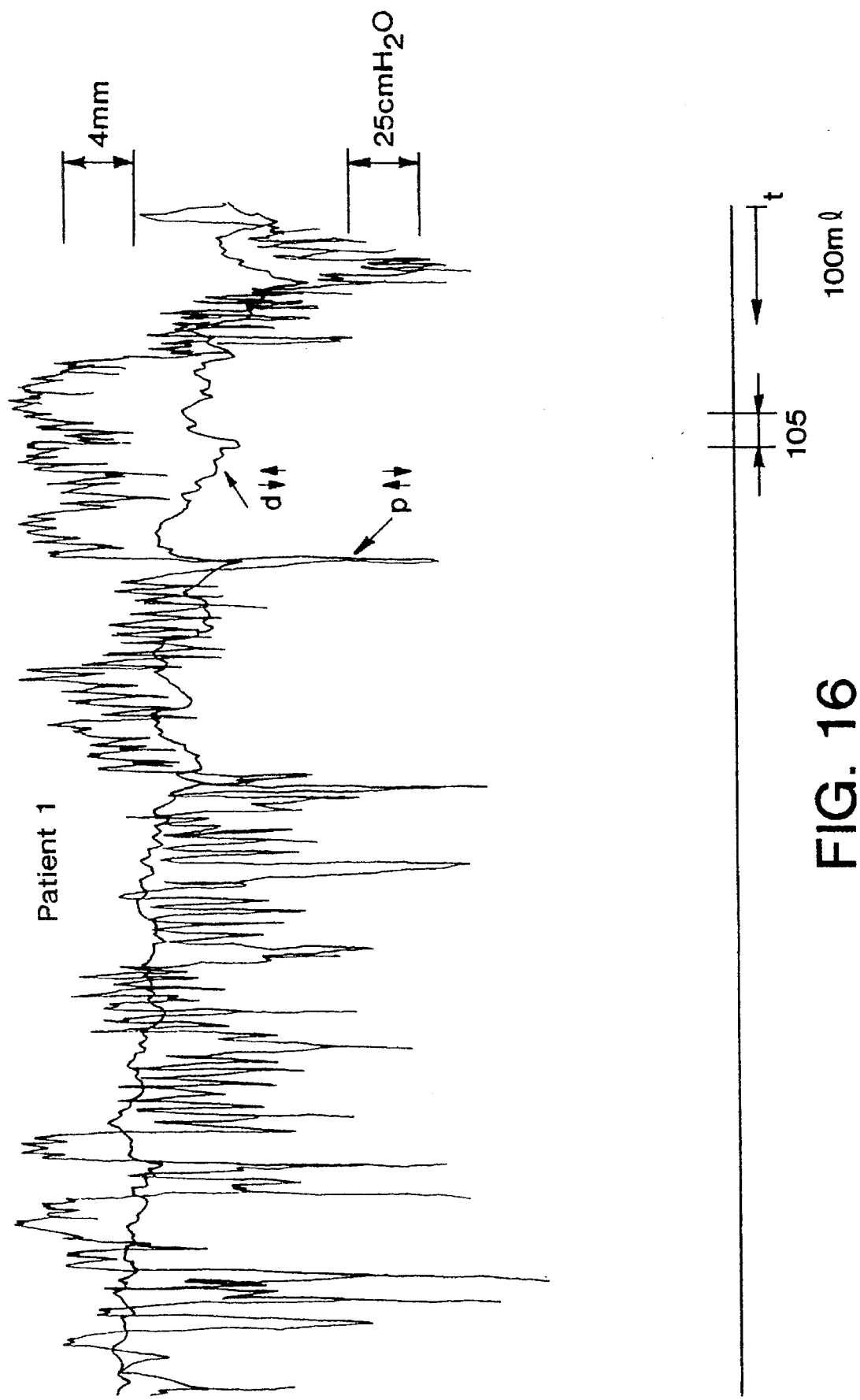
FIG. 16 is a plot of pressure and distance signals obtained during in vivo testing of Patient No. 1.

The balloon was filled with saline (20° C.) to volumes of respectively 50 ml, 100 ml and 200 ml. FIG. 16 shows a part of the recording when the bladder was filled to 200 ml. The recording of the bladder pressure is disturbed by excursion caused by respiration. Furthermore, the patient had problems lying quietly, so that artifacts are superimposed on the curves of bladder pressure. It is remarkable that artifacts caused by respiration and by bodily motions are considerably less in the micromotion (d-) signal than in the pressure signal. Nevertheless, in most cases, micromotions in the bladder wall corresponds to simultaneous variation of the bladder pressure. The recording shows that the motions can be coincident with pressure waves, in phase and in antiphase, or not coincident.

Patient No. 2 (Complaint: urge and painful micturition)

Figure 17:
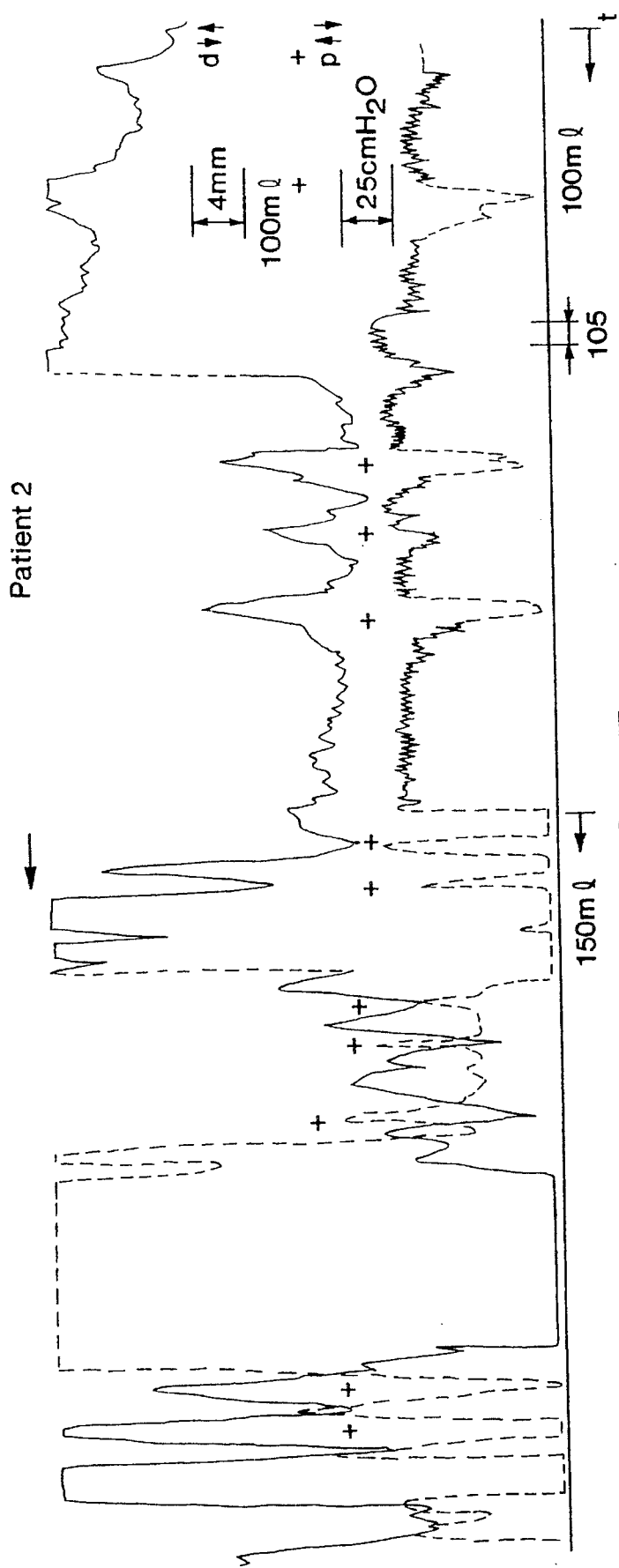
FIG. 17 is a plot of pressure and distance signals obtained during in vivo testing of Patient No. 2.

The recording of FIG. 17 shows bladder pressure and motion at the volumes of 100 ml and 150 ml, respectively. In the bladder pressures readings, we recognize variations due to respiration which, however, are not seen in motion. The patient sensed urge already at the small volume of 50 ml. The moments she felt urge, we marked on the recording. At a volume of 100 ml, large p- waves and d- waves are to be seen. It is remarkable that most of the time p- and d- waves are in phase. This makes it likely that a large part of the bladder wall, including the part we observed, is spontaneous synchronous active and in phase. This may explain the low volume level for the sensation of urge.

Patient No. 3 (Complaint: low abdominal cramps)

Figure 18A:
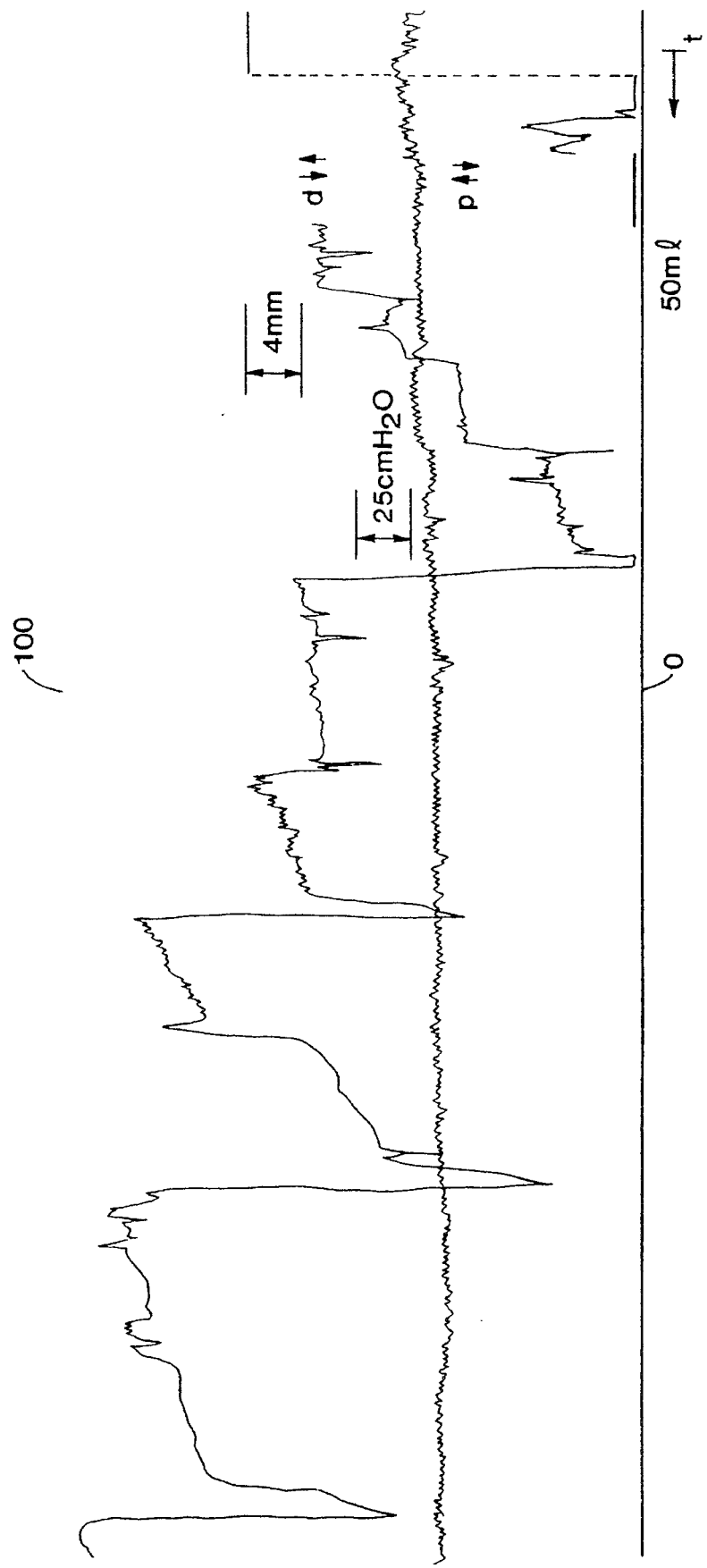
FIGS. 18A, 18B and 18C are plots of pressure and distance signals obtained during in vivo testing of Patient No. 3 at varying filling volumes (50 ml, 100 ml, 150 ml and again at 100 ml).
Figure 18B:
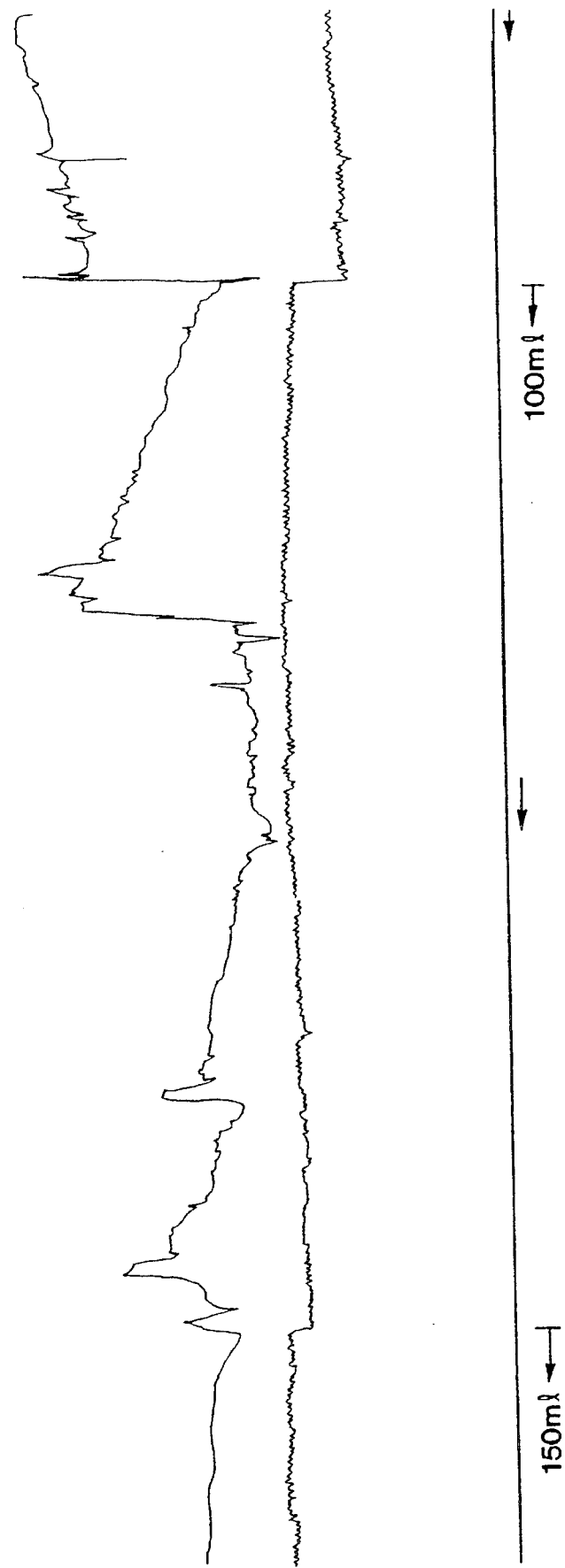
Figure 18C:
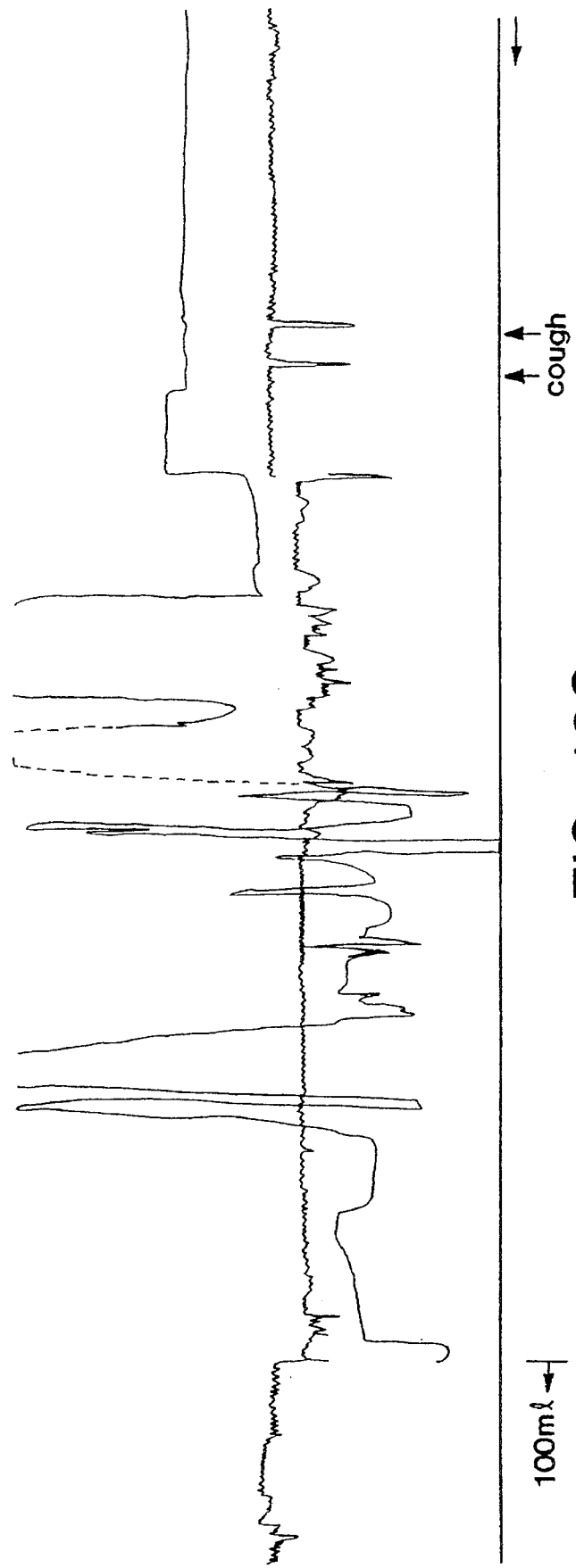

This is a very interesting case. FIGS. 18A, 18B and 18C show the recording of bladder p-signal and of d-signal at a volume of 50 ml, 100 ml, 150 ml and again 100 ml. Only a very small variation in pressure is to be seen, which is caused by respiration. As a test, the patient is asked to cough. FIG. 10C shows that the cough causes a change in p-signal but not in the d-signal. The d-signal, however, shows a large variation with an uncommon pattern. Most remarkable is that the patient reported cramps coinciding with peaks in the d-signal; peaks in contraction or dilatation. Those peaks are absent in the pressure. This measurement is convincing of the extra information that the measurement of micromotion can offer.

Patient No. 4 (Complaint: urge)

Figure 19:
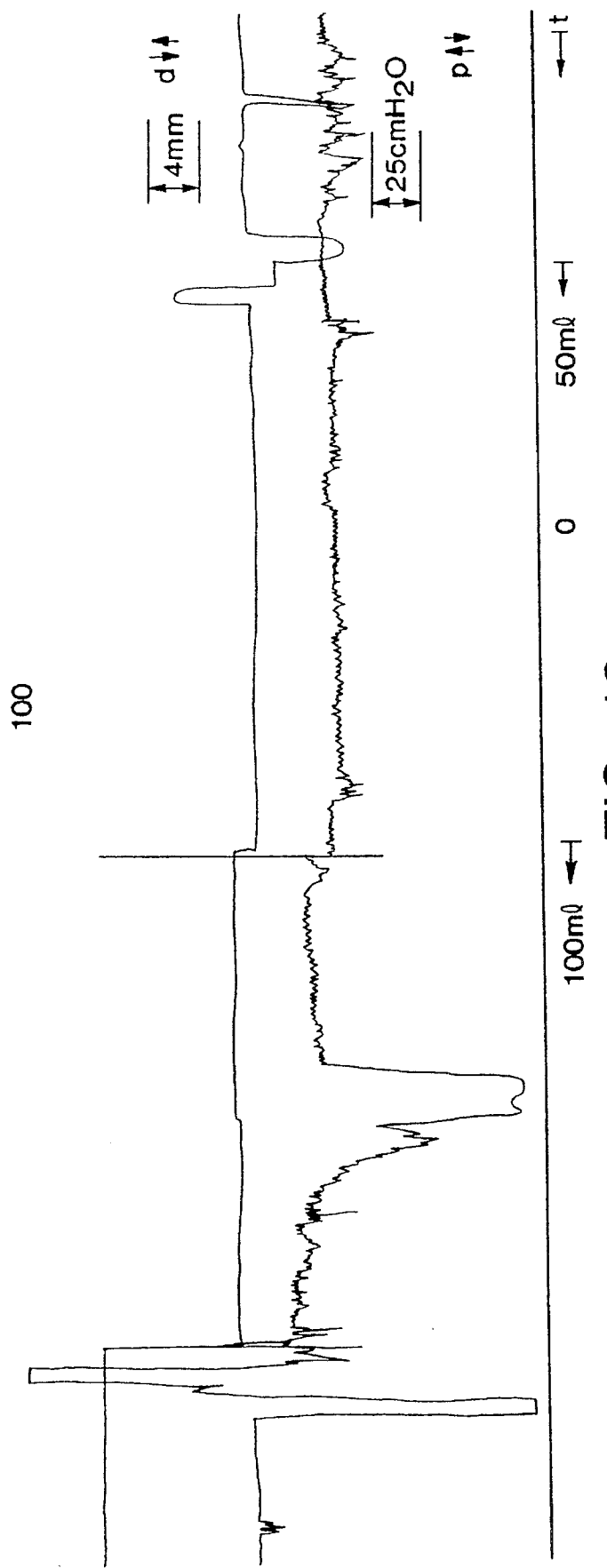
FIG. 19 is a plot of pressure and distance signals obtained during in vivo testing of Patient No. 4 at two filling volumes (50 ml and 100 ml)

The bladder is filled to 50 ml and to 100 ml. The recording is shown in FIG. 19. Again, this is an interesting result. No d-waves are observed, although the elongation during the increase in volume can be seen as a step in d. The observed part of the bladder is remarkably quiet, even when a large pressure wave is spontaneously developed. The contractions elsewhere in the bladder wall are not associated with dilatation of the observed part of the bladder. This indicates that the elasticity of the observed part is low (e.g., passive smooth muscle or connective tissue).

From the above, it can be stated that in most cases we observed spontaneous variation in detrusor pressure and motions in the wall. Two extreme situations are observed. In one extreme case, the observed part of the bladder wall obviously was a "silent" island in the wall while spontaneous contractions in other regions are responsible for spontaneous pressure waves. In another extreme case, we saw large motions in the observed part of the bladder wall while no significant pressure waves were detected. Generally speaking, the pattern of spontaneous activity in the patients is different from the pattern observed in pig bladders in vitro. All patients complained of incontinence.

Sensation of urge is associated with waves in micromotion which do not always coincide with waves in pressure and vice versa.

Finally, we conclude that the measurement of motion in the bladder wall is less affected by the varying pressure surrounding the bladder (abdominal pressure) than pressure measured in the bladder (e.g., response to cough). This is an extra merit of the measurement of motion compared to diagnosis based on measurement of detrusor pressure (=intraluminal pressure–abdominal pressure).

Thus, the present invention offers the ability to measure the distribution of variation of distances between chosen locations at the inside of the bladder wall. This can be done at different volumes of the bladders. This means that this technique can also be used to detect heterogeneity in the extension of the bladder wall during filling cystometry and to detect heterogeneity in contraction of the wall during stimulated contraction (under isovolumetric or controlled "micturition" conditions). This means that the present invention also provides a tool for fundamental research to characterize the bladder in its collection—and expulsion—phase. As previously noted, passive and active properties of the bladder tissue have been studied thoroughly on strips in vitro. Characteristics desired from such measurements, in vitro, utilizing the tissue of animals, expressed numerically, have been used to evaluate passive and contractile parameters of the human bladder, in situ, which are expressed in global terms on bladder volume and pressure. The properties derived from such in vitro experiments, however, are not representative of the in situ condition of the human bladder. In contrast, the present invention offers the possibility to derive passive and contractile properties of the human bladder, in situ, and not as global variables, but rather differentiated to local regions of the wall.

What is claimed is:

1. An apparatus for measuring the micromotion of the wall of a hollow organ comprising:

a catheter having a first end and a second end;

an inflatable balloon disposed over the first end of said catheter, said inflatable balloon being fluid tightly sealed to said catheter at a position intermediate said first and second ends;

at least four electrodes affixed to an inner surface of said balloon, said at least four electrodes being spaced apart from one another when said inflatable balloon is at least partially inflated; and a respective electrically conductive lead electrically connected to each of said at least four electrodes, each said respective electrically conductive lead having an electrically insulative covering thereover, each said respective electrically conductive lead passing through said catheter and extending beyond said second end thereof;

whereby, in use, said catheter with said deflated balloon attached is inserted into hollow organ and said balloon is at least partially inflated with a liquid having a predetermined electrical resistivity, whereby the wall of the balloon is pressed against the wall of said organ so that said electrodes will move with movement of the organ wall, whereby movement of said electrodes produces a variation in resistance between said electrodes, which is measured and compared to a calibration of the apparatus to determine the motion of the wall.

2. The apparatus according to claim 1, wherein a respective protrusion is formed on an outer surface of said balloon adjacent each of said at least four electrodes, said protrusion being forced into the wall of the hollow organ upon at least partial inflation of said balloon so as to cause movement of a respective electrode upon movement of said hollow organ wall at said protrusion.

3. The apparatus according to claim 2, further comprising means for supplying an electrically conductive solution to said catheter, at said second end, in order to at least partially inflate said balloon.

4. The apparatus according to claim 3, further comprising means for applying a voltage across a first pair of said electrically conductive leads and means for measuring an electrical resistance across a second pair of said electrically conductive leads.

5. The apparatus according to claim 4, wherein said at least four electrodes, when said balloon is inflated, are disposed radially about an axis of said catheter.

6. The apparatus according to claim 5, comprising sixteen electrodes.

7. The apparatus according to claim 6, wherein said hollow organ is a urinary bladder and said inflatable balloon is of a size to substantially fill said bladder upon inflation thereof.

* * * * *